US010550151B2

(12) United States Patent
Sessa et al.

(10) Patent No.: US 10,550,151 B2
(45) Date of Patent: *Feb. 4, 2020

(54) CELL-PENETRATING COMPOSITIONS AND METHODS USING SAME

(71) Applicant: Yale University, New Haven, CT (US)

(72) Inventors: William C. Sessa, Madison, CT (US); Frank J. Giordano, Madison, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/910,519

(22) Filed: Mar. 2, 2018

(65) Prior Publication Data

US 2018/0201649 A1  Jul. 19, 2018

Related U.S. Application Data

(63) Continuation of application No. 15/036,849, filed as application No. PCT/US2014/066619 on Nov. 20, 2014, now Pat. No. 9,908,915.

(60) Provisional application No. 61/908,963, filed on Nov. 26, 2013.

(51) Int. Cl.
| | |
|---|---|
| *A61K 38/00* | (2006.01) |
| *A61K 38/04* | (2006.01) |
| *A61K 38/16* | (2006.01) |
| *A61K 47/64* | (2017.01) |
| *C07K 14/00* | (2006.01) |
| *C07K 7/06* | (2006.01) |
| *C07K 7/00* | (2006.01) |
| *C07K 14/47* | (2006.01) |

(52) U.S. Cl.
CPC .............. *C07K 7/06* (2013.01); *A61K 47/645* (2017.08); *C07K 14/4702* (2013.01); *C07K 14/4703* (2013.01); *A61K 38/00* (2013.01); *C07K 2319/01* (2013.01)

(58) Field of Classification Search
CPC ........ A61K 38/00; A61K 38/04; A61K 38/16; A61K 47/645; A61K 47/64; C07K 14/4702; C07K 14/4703; C07K 2319/01; C07K 7/06
USPC ........... 514/1.1, 21.3, 21.4, 21.5, 21.6, 21.7, 514/21.8; 530/324, 325, 326, 327, 328, 530/329, 330
See application file for complete search history.

(56) References Cited

U.S. PATENT DOCUMENTS

| | | | |
|---|---|---|---|
| 7,473,531 B1 | 1/2009 | Domon et al. | |
| 7,494,976 B2 * | 2/2009 | Sessa .................. | C07K 14/4702 514/1.1 |
| 7,833,967 B2 | 11/2010 | Hogenhaug | |
| 7,981,866 B2 | 7/2011 | Ma et al. | |
| 8,487,072 B2 | 7/2013 | Beliveau et al. | |
| 2003/0165510 A1 | 9/2003 | Sessa et al. | |
| 2005/0181474 A1 | 8/2005 | Giordano et al. | |
| 2009/0226372 A1 | 9/2009 | Ruoslahti et al. | |
| 2011/0218152 A1 | 9/2011 | Beliveau et al. | |

FOREIGN PATENT DOCUMENTS

| | | |
|---|---|---|
| JP | 2011514160 A | 5/2011 |
| WO | 0220768 A2 | 3/2002 |
| WO | 03064614 A2 | 8/2003 |
| WO | 2009105671 A2 | 8/2009 |
| WO | 2010030813 A2 | 3/2010 |
| WO | 2013184482 A1 | 12/2013 |

OTHER PUBLICATIONS

A0A0A9JLM5 from UniProt, pp. 1-3. Integrated into UniProtKM/TrEMBL Mar. 4, 2015.
European Search Report for European Patent Application No. 14866083.0 dated Apr. 21, 2017.
PCT International Search Report and Written Opinion for PCT International Application No. PCT/US2014/066619 dated Feb. 25, 2015.
Carriere, et al.,Inhibition of protein synthesis by aminoglycoside-arginine conjugates., RNA. 8 (10) ,2002 ,1267-1279.
Collawn, et al.,An analysis of the physical properties of peptides that influence the pigeon cytochrome c specific T lymphocyte response, Mol Immunol. 26(11) ,1989 ,1069-1079.
Giordano, et al.,From combinatorial peptide selection to drug prototype (I): targeting the vascular endothelial growth factor receptor pathway, Proc Natl Acad Sci U S A. 107(11) ,2010 ,5112-5117.
Lidington, et al.,A role for proteinase-activated receptor 2 and PKC-epsilon in thrombin-mediated induction of decay-accelerating factor on human endothelial cells, Am J Physiol Cell Physiol. 289(6) ,2005 ,C1437-C1447.

* cited by examiner

*Primary Examiner* — Julie Ha
(74) *Attorney, Agent, or Firm* — Saul Ewing Arnstein & Lehr LLP; Kathryn Doyle; Justin Crotty

(57) ABSTRACT

An isolated transport peptide, which crosses the cell membrane of a cell and/or binds to a target cell is described. The transport peptide can be incorporated into a transport construct in which the transport peptide is linked to a cargo moiety to be delivered into a cell. Also described herein is a method of delivering a transport construct into and/or to a cell.

4 Claims, 8 Drawing Sheets
Specification includes a Sequence Listing.

Live HUVEC - 1 hr pulse

Live HUVEC - 3 hr chase

CELL-PENETRATING COMPOSITIONS AND METHODS USING SAME

CROSS-REFERENCE TO RELATED APPLICATIONS

The present application is a continuation of, and claims priority to, U.S. patent application Ser. No. 15/036,849, filed May 16, 2016, now allowed, which is a 35 U.S.C. § 371 national phase application from, and claims priority to, International Application No. PCT/US2014/066619, filed Nov. 20, 2014, and published under PCT Article 21(2) in English, which claims priority under 35 U.S.C. § 119(e) to U.S. Provisional Patent Application No. 61/908,963, filed Nov. 26, 2013, all of which applications are incorporated herein by reference in their entireties.

STATEMENT REGARDING FEDERALLY SPONSORED RESEARCH OR DEVELOPMENT

This invention was made with government support under HL064793, HL061371, HL096670 and HL081190 awarded by National Institutes of Health. The government has certain rights in the invention.

BACKGROUND OF THE INVENTION

The cell membrane (also known as the plasma membrane or cytoplasmic membrane) is a biological membrane that separates the interior of the cell from the outside environment, protecting the cell from its surroundings. The membrane comprises a phospholipid bilayer with embedded proteins, and is involved in cellular processes such as cell adhesion, ion conductivity and cell signaling.

The cell membrane controls the movement of substances in and out of cells and is selectively permeable to ions and organic molecules. The movement of substances across the membrane may be passive (i.e., occurring without the input of cellular energy) or active (i.e., requiring the cell to expend energy in transporting it). The cell membrane thus works as a selective filter, employing transport mechanisms such as passive osmosis and diffusion, transmembrane protein channels transportation, endocytosis and exocytosis.

Intracellular delivery of biologically active compounds is challenging because the cell membrane is remarkably impermeable to extracellular polar compounds. There is thus much interest in identifying novel cell-permeable peptides ("CPPs") that can act as "Trojan horses" for carrying cargo molecules inside living cells. CPPs have been employed in intracellular delivery of oligonucleotides (Astriab-Fisher et al., 2000, Biochem. Pharmacol. 60:83-90; Eguchi et al., 2001, J. Biol. Chem. 276:26204-26210), plasmids (Morris et al., 1999, Nucleic Acids Res. 27:3510-3517), viruses (Gratton et al., 2003, Nat. Med. 9:357-362), peptides (Gratton et al., 2003, Nat. Med. 9:357-362; Soomets et al., 2000, Biochim. Biophys. Acta 1467:165-176) and fluorophores (Bucci et al., 2000, Nat. Med. 6:1362-1367). The Antennapedia homeodomain ("AP"; a 16-amino acid peptide, which is a *Drosophila* transcription factor), as well as the HIV transactivator of transcription ("TAT"; 15 amino acids) are amongst the first CPPs described, along with more recently described CPP sequences, such as poly-Arginine ($Arg_7$ or $Arg_9$) and C105Y (a 17-amino acid peptide).

The capacity of CPPs to translocate cargo into cells could make them attractive delivery agents for cell-impermeable therapeutic compounds. However, the therapeutic effect, kinetics, safety profile and specificity of CPPs in humans are still unknown. Novel target-engineered CPPs with enhanced internalization capabilities, enhanced overall therapeutic efficacy and safety, minimal peptide elimination/degradation and high therapeutic activity/cost ratio are required.

Caveolins are cholesterol binding proteins that may regulate signal transduction pathways (Smart et al., 1999, Mol. Cell. Biol. 19:7289-7304; Kurzchalia & Parton, 1999, Curr. Opin. Cell. Biol. 11:424-431). Recent studies have focused on their subcellular trafficking and regulation of endothelial nitric oxide synthase (eNOS). eNOS-derived NO is necessary for the maintenance of systemic blood pressure, vascular remodeling, angiogenesis and wound healing (Huang et al., 1995, Nature 377:239-242; Murohara et al., 1998, J. Clin. Invest. 101:2567-2578; Rudic et al., 1998, J. Clin. Invest. 101:731-736; Lee et al., 1999, Am. J. Physiol. 277:HI600-1608). eNOS can physically interact with caveolin-1 and caveolin-3 by binding to their putative scaffolding domain located between residues 82-101 (Li et al., 1996, J. Biol. Chem. 271:29182-29190), and this interaction renders eNOS in its "less active" state (Garcia-Cardena et al., 1997, J. Biol. Chem. 272:25437-25440; Ju et al., 1997, J. Biol. Chem. 272:18522-18525; Michel et al., 1997, J. Biol. Chem. 272:25907-25912). Consistent with the model of caveolin as a negative regulator of eNOS, peptides derived from the scaffolding domain of caveolin-1 disrupt the binding of eNOS to caveolin and inhibit NOS activity in a dose dependent manner in vitro ($IC_{50}$=1-3 μM) by slowing electron flux from the reductase to the oxygenase domain of NOS (Garcia-Cardena et al., 1997, J. Biol. Chem. 272:25437-25440; Ju et al., 1997, J. Biol. Chem. 272:18522-18525; Ghosh et al., 1998, J. Biol. Chem. 273:22267-22271).

There is a need in the art to identify novel molecules that efficiently penetrate cell membranes. Such molecules would be useful in promoting the delivery of cargo moieties, such as therapeutic agents, nucleic acids, peptides, saccharides, lipids, liposomes and such, across the cell membrane. The present invention satisfies this unmet need.

BRIEF SUMMARY OF THE INVENTION

The invention provides an isolated transport peptide, or a salt or solvate thereof, comprising the amino acid sequence RRPPR (SEQ ID NO: 1).

The invention further provides an isolated transport construct, or a salt or solvate thereof, comprising a transport peptide comprising SEQ ID NO: 1 linked to a cargo moiety.

The invention further provides an isolated transport construct, or a salt or solvate thereof, comprising a transport peptide comprising SEQ ID NO:1 that is linked to a cargo moiety comprising the sequence selected from the group consisting of SEQ ID NOs: 3-6.

The invention further provides a composition comprising an isolated nucleic acid encoding a transport peptide comprising SEQ ID NO: 1.

The invention further provides a composition comprising an isolated nucleic acid encoding a transport peptide comprising SEQ ID NO: 1, further comprising an additional nucleic acid encoding at least one cargo moiety selected from the group consisting of SEQ ID NOs: 3-6.

The invention further provides a vector comprising a nucleic acid encoding a transport peptide comprising SEQ ID NO: 1.

The invention further provides an isolated host cell comprising exogenous nucleic acid encoding a transport peptide comprising SEQ ID NO: 1.

The invention further provides a method of delivering a cargo moiety (in)to a target cell.

The invention further provides a method of delivering a cargo moiety (in)to a target cell of a subject in need thereof.

In certain embodiments, the transport peptide consists of SEQ ID NO: 1. In other embodiments, the transport peptide and/or construct is/are part of a pharmaceutical composition further comprising a pharmaceutically acceptable carrier. In yet other embodiments, the cargo moiety is at least one selected from the group consisting of a nucleic acid; peptide; protein; oligosaccharide; lipid; glycolipid; lipoprotein; small molecule compound; therapeutic drug; UV-vis, fluorescent or radioactive label; imaging agent; diagnostic agent; prophylactic agent; liposome and virus. In yet other embodiments, the nucleic acid comprises 5'-CGGCGCCCGC-CTCGT-3' (SEQ ID NO: 7). In yet other embodiments, the composition comprises a nucleic acid encoding a transport construct selected from the group consisting of SEQ ID NO: 1-SEQ ID NO: 3; SEQ ID NO: 1-SEQ ID NO: 4; SEQ ID NO: 1-SEQ ID NO: 5; SEQ ID NO: 1-SEQ ID NO: 6; SEQ ID NO: 3-SEQ ID NO: 1; SEQ ID NO: 4-SEQ ID NO: 1; SEQ ID NO: 5-SEQ ID NO: 1; and SEQ ID NO: 6-SEQ ID NO: 1. In yet other embodiments, the composition further comprises a nucleic acid encoding at least one cargo moiety selected from the group consisting of a peptide; a protein; a biologically active compound; a label; an imaging agent; a diagnostic agent; a therapeutic agent; and a prophylactic agent.

In certain embodiments, the cargo moiety is covalently linked to the transport peptide through a linker or a chemical bond. In other embodiments, the linker comprises a disulfide bond, or the chemical bond between the cargo moiety and the transport peptide comprises a disulfide bond. In yet other embodiments, the cargo moiety comprises a peptide moiety. In yet other embodiments, the cargo moiety comprises a peptide or protein. In yet other embodiments, the transport peptide is covalently linked through an amide bond to the N-terminus of the peptide moiety of the cargo moiety. In yet other embodiments, the transport peptide is covalently linked through an amide bond to the C-terminus of the peptide moiety of the cargo moiety.

In certain embodiments, the transport construct comprises at least one sequence selected from the group consisting of SEQ ID NO: 1-SEQ ID NO: 3; SEQ ID NO: 1-SEQ ID NO: 4; SEQ ID NO: 1-SEQ ID NO: 5; SEQ ID NO: 1-SEQ ID NO: 6; SEQ ID NO: 3-SEQ ID NO: 1; SEQ ID NO: 4-SEQ ID NO: 1; SEQ ID NO: 5-SEQ ID NO: 1; and SEQ ID NO: 6-SEQ ID NO: 1. In other embodiments, the transport construct is selected from the group consisting of SEQ ID NO: 1-SEQ ID NO: 3; SEQ ID NO: 1-SEQ ID NO: 4; SEQ ID NO: 1-SEQ ID NO: 5; SEQ ID NO: 1-SEQ ID NO: 6; SEQ ID NO: 3-SEQ ID NO: 1; SEQ ID NO: 4-SEQ ID NO: 1; SEQ ID NO: 5-SEQ ID NO: 1; and SEQ ID NO: 6-SEQ ID NO: 1.

In certain embodiments, the vector further comprises transcriptional activation elements that allow for the expression of the nucleic acid encoding the transport peptide. In other embodiments, the vector comprises a nucleic acid encoding a cargo moiety in-frame with the nucleic acid encoding the transport peptide. In yet other embodiments, the nucleic acid is a vector comprising (a) a nucleic acid encoding the transport peptide, and (b) a nucleic acid encoding a cargo moiety in-frame with the nucleic acid encoding the transport peptide. In yet other embodiments, the host cell further comprises transcriptional activation elements that allow for the expression of the nucleic acid of (a) and the nucleic acid of (b) in the host cell.

In certain embodiments, the transport peptide binds to a target cell and/or crosses a cell membrane. In other embodiments, the transport construct binds to a target cell and/or crosses a cell membrane. In yet other embodiments, the target cell comprises at least one selected from the group consisting of an endothelial cell, cardiac cell, immune cell, skeletal muscle cell and brain cell. In yet other embodiments, the cell is mammalian. In yet other embodiments, the mammal is human.

In certain embodiments, the method comprises contacting the target cell with a transport construct, wherein the transport construct comprises a cargo moiety linked a transport peptide comprising SEQ ID NO: 1, whereby the cargo moiety is delivered to or into the target cell.

In certain embodiments, the method comprises contacting the target cell with a transport construct, wherein the transport construct comprises a transport peptide comprising SEQ ID NO:1 linked to a cargo moiety comprising a sequence selected from the group consisting of SEQ ID NOs: 3-6, whereby the cargo moiety is delivered to or into the target cell.

In certain embodiments, the method comprises administering to the subject a therapeutically effective amount of a transport construct, wherein the transport construct comprises the cargo moiety linked to a transport peptide comprising SEQ ID NO: 1, whereby the cargo moiety is delivered to or into the target cell of the subject.

In certain embodiments, the method comprises administering to the subject a therapeutically effective amount of a transport construct, wherein the transport construct comprises a transport peptide comprising SEQ ID NO:1 that is linked to a cargo moiety comprising a sequence selected from the group consisting of SEQ ID NOs: 3-6, whereby the cargo moiety is delivered to or into the target cell of the subject.

In certain embodiments, a compound and/or composition of the invention is/are administered to the subject by at least one route selected from the group consisting of oral, transmucosal, topical, transdermal, intradermal, subcutaneous, ophthalmic, intravitreal, subconjunctival, suprachoroidal, intracameral, inhalational, intrabronchial, pulmonary, intravenous, intra-arterial, intraduodenal, intravesical, parenteral, intrathecal, intramuscular and intragastrical.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIG. 2A: Endo5-Cav completely blocked VEGF-induced NO release. Cultured BAEC were pretreated for 6 hours with the indicated peptides ($10^{-5}$ M) and stimulated with VEGF ($10^{-9}$ M) for 30 min as indicated. *$P<0.05$ compared with vehicle, and †$P<0.05$ compared with AP-Cav+VEGF. n=4 in triplicate.

FIG. 2B: AP-Cav and Endo5-Cav showed a dose-dependent effect. Cultured BAEC were pretreated with peptides (1-50× $10^{-6}$ M) for 6 hours and stimulated with VEGF as described in FIG. 2A. *$P<0.05$ compared with vehicle, and †$P<0.05$ compared with AP-Cav+VEGF. n=4 in duplicate. FIG. 2C: AP-Cav and Endo5-Cav showed time dependent effects. BAEC were treated with peptides ($10^{-5}$ M) for 1, 2, 4 or 6 hours, and stimulated with VEGF as described in FIG. 2A. *$P<0.05$ compared with vehicle, and †$P<0.05$ compared with AP-Cav+VEGF. n=4 in duplicate. FIG. 2D: Optimization of both the cell-penetrating sequence and Cav domain of AP-Cav led to a shorter, more potent eNOS inhibitor. Substitution of AP to Endo5 and shortening of Cav(82-101) to CavAB(82-95) (Endo5-CavAB; $10^{-5}$ M) completely blocked VEGF-induced NO release, whereas Endo5-CavAB ($2\times10^{-6}$ M), a much shorter peptide at a lesser dose, had a similar effect to AP-Cav ($10^{-5}$ M).

FIG. 3A: Pretreatment of mice with AP-Cav (1 mg/kg) or Endo5-Cav (same dose on a molar basis) for 1 hour prevented mustard oil-induced increase in vascular permeability (right ear; 30 min), whereas control peptides had no significant effect. Left ears were painted with mineral oil alone (vehicle) and considered as baseline control. Mice were pre-injected with Evans blue. *$P<0.05$ compared with control peptide, and †$P<0.05$ compared with AP-Cav+mustard oil. n=6 or 8 per group in duplicate. FIG. 3B: Representative values for the data presented in FIG. 3A are illustrated.

FIG. 4A: Fluorescence readouts for similar concentration of rhodamine-AP (rhod-AP) and carboxyfluorescein-Endo5 (cFluo-Endo5) dissolved in the same cell lysis solution used in FIG. 4B were performed to confirm the linearity between peptide concentration in solution and fluorescence values. Peptides were used separately to prevent interference. FIG. 4B: Carboxyfluorescein-Endo5 rate of internalization is greater than that of rhodamine-AP. Cultured BAEC were incubated for 1, 2, 4 or 6 hours with individual peptides, acid washed, rinsed, trypsinized, lysed and total internal fluorescence was determined and converted to moles of peptides per $10^6$ by using a standard curve. Cells incubated with peptides for 5 min and treated as described were used as background for non-internalized staining.

FIG. 5A: Cultured HUVEC were treated with carboxyfluorescein-Endo5 (green) or rhodamine-AP (red; $10^{-5}$ M) for 1 hour (pulse), rinsed and live imaging in unfixed cells was performed using an epifluorescence microscope. Note the punctate staining with both peptides and the absence of nuclear staining (oval-shaped dark zone). Merged images showed localization (yellow) between both peptides. Representative cells shown. FIG. 5B: After treatment described in FIG. 5A, peptide localization was chased for two hours in live HUVEC and visualized. Colocalization (yellow) between both peptides was still observable. FIG. 5C: Endo5 and AP prevented AP-Cav and Endo5-Cav inhibition of VEGF-induced NO release. Cultured BAEC were pretreated with either AP or Endo5 ($5\times10^{-5}$ M) and incubated for 6 h with either AP-Cav or Endo5-Cav ($10^{-5}$ M) and stimulated with VEGF as described in FIG. 2. *$P<0.05$ compared with vehicle n=6 per group in triplicate.

DETAILED DESCRIPTION OF THE INVENTION

Figure 1:
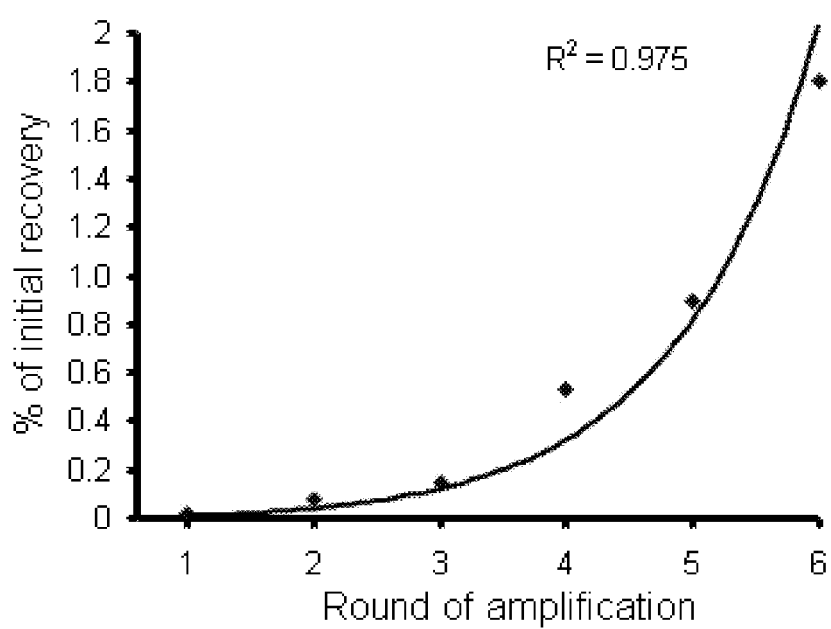
FIG. 1 is a graph illustrating the exponential enrichment of cell-permeable phage during biopanning. The percentages of recovered phage from Table 1 are plotted for the six rounds of biopanning in endothelial cells ("EC"). Exponential correlation is established with a $R^2$ value of 0.975.

The invention relates in part to the unexpected identification of Endo5 (RRPPR; SEQ ID NO: 1), a short five-amino acid peptide, as a cell-permeable peptide (CPP).

In certain embodiments, Endo5 is a transport peptide that crosses the cell membrane. In other embodiments, once a cargo moiety is linked to Endo5, the resulting construct crosses the cell membrane more efficiently than the cargo moiety itself. In certain embodiments, the cargo moiety is selected from the group consisting of a nucleic acid; peptide; protein; oligosaccharide; lipid; glycolipid; lipoprotein; small molecule compound; therapeutic drug; UV-vis, fluorescent or radioactive label; imaging agent; diagnostic agent; prophylactic agent; liposome and virus. In other embodiments, the cargo moiety is linked to the transport peptide through a covalent or non-covalent linkage.

As demonstrated herein, Endo5, a short pentapeptide, was unexpectedly isolated using a phage display library-based approach. Endo5 was selected for its capacity to increase phage internalization in human endothelial cells. Functional analyses revealed that Endo5-Cav was more potent than AP-Cav at inhibiting vascular endothelial growth factor (VEGF)-induced nitric oxide release in endothelial cells in vitro and permeability in vivo. Pharmacokinetic and competition studies showed that Endo5 was internalized by endothelial cells at a greater rate than AP, and that Endo5-Cav activities were competitively inhibited by AP, providing evidence for the similarity of Endo5 and AP uptake pathways. As supported by the data reported herein, Endo5 is not only the shortest CPP sequence known at the time of the invention, but also as the first CPP engineered specifically for high internalization rates in endothelial cells.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, non-limiting methods and materials are described.

The articles "a" and "an" are used herein to refer to one or to more than one (i.e., to at least one) of the grammatical object of the article. By way of example, "an element" means one element or more than one element.

As used herein, the term "about" when referring to a measurable value such as an amount, a temporal duration, and the like, is meant to encompass variations of ±20% or ±10%, more specifically ±5%, even more specifically ±1%, and still more specifically ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

The term "amino acid sequence variant" refers to polypeptides having amino acid sequences that differ to some extent from a native sequence polypeptide. Ordinarily, amino acid sequence variants will possess at least about 70% homology, at least about 80% homology, at least about 90% homology, at least about 95% homology, at least about 96% homology, at least about 97% homology, at least about 98% homology, or at least about 99% homology to the native polypeptide. The amino acid sequence variants possess substitutions, deletions, and/or insertions at certain positions within the amino acid sequence of the native amino acid sequence.

As used herein, the term "AP" refers to the Antennapedia homeodomain (a 16-amino acid peptide that is a *Drosophila* transcription factor), which is the peptide of SEQ ID NO: 2 or a salt or solvate thereof.

As used herein, the term "BAEC" refers to bovine aorta endothelial cell(s).

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are complementary. A common model is the "lock-and-key" used to describe how enzymes fit around their substrate. In a non-limiting example, the binding of the caveolin protein may occur at one or more domains of eNOS, such as, but not limited to, the oxygenase domain of eNOS and/or the reductase domain of eNOS.

As used herein, the term "caveolin scaffolding domain" refers to domains inclusive of putative scaffolding domains of any caveolin protein. Thus, the term as used herein is not limited to putative scaffolding domains. The complete amino acid sequence of human Cav-1 may be found at GenBank Accession No. BAG70230.1 (SEQ ID NO: 3). The complete protein code for human Cav-3 may be found at GenBank Accession No. AAC39758.1 (SEQ ID NO: 4).

Examples of caveolin scaffolding domains include, but are not limited to, the following: amino acids 82-101 of human caveolin-1 ($^{82}$DGIWKASFTTFTVTKYWFYR$^{101}$) (SEQ ID NO: 5) or equivalents thereof amino acids 82-95 of human caveolin-1 ($^{82}$DGIWKASFTTFTVT$^{95}$) (SEQ ID NO: 6) or equivalents thereof.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties. Specific examples of binding domains include, but are not limited to, DNA binding domains and ATP binding domains.

As used herein, the term "EC" refers to endothelial cell(s).

As used herein, the term "Endo5" refers to the peptide of SEQ ID NO: 1 or a salt or solvate thereof.

As used herein, the term "Evans blue" refers to any salt or solvate of (6E,6'E)-6,6-[(3,3'-dimethylbiphenyl-4,4'-diyl) di(1E)hydrazin-2-yl-1-ylidene]bis(4-amino-5-oxo-5,6-dihydronaphthalene-1,3-disulfonate).

As used herein, the term "heterologous peptide" refers to any peptide, polypeptide or protein whose sequence is selected in such a way that the product of the fusion of this sequence with the membrane translocation domain has a sequence different from the wild-type sequence flanking any membrane translocation domain.

As used herein, the term "membrane translocation domain" refers to a peptide capable of permeating the membrane of a cell and which is used to transport attached peptides into a cell in vivo.

As used herein, the term "patient," "individual" or "subject" refers to a human or a non-human mammal. Non-human mammals include, for example, livestock and pets, such as ovine, bovine, porcine, canine, feline and murine mammals. In certain embodiments, the patient, individual or subject is human.

As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the term "pharmaceutical composition" or "composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, inhalational, rectal, vaginal, transdermal, intranasal, buccal, sublingual, parenteral, intrathecal, intragastrical, ophthalmic, pulmonary and topical administration. In certain embodiments, routes of administration include transdermal, transmucosal (e.g., sublingual, lingual, (trans)buccal, (trans) urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, pleural, peritoneal, subcutaneous, epidural, otic, intraocular, and/or topical administration As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate;

powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, metallic salts including ammonium salts and alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the terms "pharmaceutically effective amount" and "effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "PNA" refers to a peptide nucleic acid.

As used herein, the term "polypeptide" refers to a polymer composed of amino acid residues, related naturally occurring structural variants, and synthetic non-naturally occurring analogs thereof linked via peptide (or amide) bonds. Synthetic polypeptides may be synthesized, for example, using an automated polypeptide synthesizer.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "protein" typically refers to large polypeptides.

As used herein, the term "RHMVEC" refers to rat heart microvascular endothelial cell(s).

As used herein, the term 'solvate' refers to a complex between a molecule and a solvent molecule, which may exist in solution or in solid phase. In certain embodiments, the solvent comprises at least one selected from the group consisting of water, methanol, ethanol, n-propanol, 2-propanol, DMSO, DMF, ethyl ether, acetone and pyridine.

As used herein, the term "transport construct" refers to a construct that crosses the cell membrane, wherein the construct comprises the transport peptide and at least one cargo moiety, wherein the cargo moiety crosses the cell membrane at a lower rate or to a lower degree than the transport construct. In certain embodiments, the cargo moiety is selected from the group consisting of a nucleic acid; peptide; protein; oligosaccharide; lipid; glycolipid; lipoprotein; small molecule compound; therapeutic drug; UV-vis, fluorescent or radioactive label; imaging agent; diagnostic agent; prophylactic agent; liposome and virus. In other embodiments, the cargo moiety is linked to the transport peptide through a covalent or non-covalent linkage.

As used herein, the term "transport peptide" or "CPP" refers to a cell-permeable peptide, which is defined as a peptide capable of permeating and/or crossing a cell membrane.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The invention relates to the unexpected finding that Endo5, a short pentapeptide (RRPPR), is a very potent CPP. As described herein, Endo5 was isolated though a competitive selection process for its capacity to be quickly internalized by vascular endothelial cells. Endo5 was further shown to increase cargo uptake by cells and increase therapeutic activity of a cargo to which it is conjugated.

As described herein, Endo5 was the most highly enriched randomly generated peptide when expressed at the surface of phages selected for the ability to be quickly internalized by endothelial cells. The maximum potency of Endo5-Cav at inhibiting VEGF-induced NO release was greater than that of AP-Cav on a similar molar basis. Further, despite its smaller size (Endo5 is a 5-mer peptide vs AP is a 16-mer acid peptide), the rate of uptake of Endo5 was three times greater than that of AP. Endo5-Cav was found to be more potent than AP-Cav at inhibiting vascular permeability in vivo.

Mechanistically, the cellular pathways involved in Endo5 uptake appear similar to that of AP. This is supported by the following findings: significant co-localization between Endo5 and AP during initial endocytosis and intracellular distribution; the competitive inhibition of Endo5-Cav effect by AP, and the competitive inhibition of AP-Cav activity by Endo5. The findings reported herein provide evidence for Endo5 higher "internalization efficiency per amino acid" abilities compared to the well-established AP.

The rationale for designing a potent CPP for an endothelial cell resides not only in the various diseases characterized by aberrant endothelial cell activity, but also from the strategic localization of endothelial cells between the blood and underlying tissues. Following absorption, drug distribution through the vascular compartment may be quickly impaired though elimination and degradation. These normal drug inactivation mechanisms may be offset by rapid internalization at the site of action. Evidence of the magnitude of Endo5 internalization in endothelial cells, compared to the pool of randomly generated CPP the present system allows to test, is illustrated by its capacity to promote phage uptake in the T7 select system. This system favors rapid uptake exclusively through high affinity binding to endothelial cells, since it allows the surface expression of less than one peptide copy per phage. In certain embodiments, Endo5 is the first CPP engineered specifically for high endothelial cell internalization though the competitive selection approach.

Without wishing to be limited by any theory, the intracellular distribution of cargos towards their target may be at least partially, independent of the CPP sequence based on the fact that Cav fused to two completely different CPPs (Endo5 or AP) attenuated eNOS activity, inhibited vascular permeability and co-localized after a two-hour "chase." Further, it is possible that Endo5, as well as other CPP, may allow various exit pathways from internalization organelles and/or direct the intracellular localization of cargo molecules differently. However, the difference in uptake rate between Endo5 and AP is the likely mechanism to rationalize the difference in potency between Endo5-Cav and AP-Cav. This is also supported by the data documenting the similar localization of Endo5 and AP in live cells. On the other hand, the increase in Cav potency when fused to Endo5 and the near saturation of AP-Cav effect on eNOS activity at high doses suggest that AP-Cav effect might be limited by an overlapping rate of internalization and elimination/degradation rather than by a limitation of the pharmacophore (Cav). Without wishing to be limited by any theory, this highlights the interest in identifying highly potent CPP sequences, such as sequences comprising Endo5.

Compositions

The invention includes an isolated transport peptide that crosses a cell membrane. In certain embodiments, the peptide, or a salt or solvate thereof, comprises the amino acid sequence RRPPR (SEQ ID NO: 1). In other embodiments, the transport peptide, or a salt or solvate thereof, consists essentially of SEQ ID NO: 1. In yet other embodiments, the transport peptide, or a salt or solvate thereof, consists of SEQ ID NO: 1. In yet other embodiments, the transport peptide binds to a target cell or crosses a cell membrane. In yet other embodiments, the cell comprises an endothelial cell, cardiac cell, immune cell, skeletal muscle cell or brain cell. In yet other embodiments, the cell consists of an endothelial cell, cardiac cell, immune cell, skeletal muscle cell or brain cell.

The invention further provides a pharmaceutical composition comprising a transport peptide comprising SEQ ID NO: 1 and a pharmaceutically acceptable carrier.

In certain embodiments, the compositions of the invention further comprise a pharmaceutically acceptable carrier.

In certain embodiments, the transport construct comprises a cargo moiety linked to a transport peptide comprising SEQ ID NO: 1. In other embodiments, the transport peptide consists of SEQ ID NO: 1. In yet other embodiments, the cargo moiety is at least one selected from the group consisting of a nucleic acid (and analogues thereof, such as a peptide nucleic acid or "PNA"); peptide; protein; oligosaccharide; lipid; glycolipid; lipoprotein; therapeutic drug; UV-vis, fluorescent or radioactive label; imaging agent; diagnostic agent; prophylactic agent; liposome and virus (such as T-7 bacteriophage).

In certain embodiments, the cargo moiety is at least one selected from the group consisting of SEQ ID NOs: 3-6. In other embodiments, the transport construct comprises at least one sequence selected from the group consisting of SEQ ID NO: 1-SEQ ID NO: 3; SEQ ID NO: 1-SEQ ID NO: 4; SEQ ID NO: 1-SEQ ID NO: 5; SEQ ID NO: 1-SEQ ID NO: 6; SEQ ID NO: 3-SEQ ID NO: 1; SEQ ID NO: 4-SEQ ID NO: 1; SEQ ID NO: 5-SEQ ID NO: 1; and SEQ ID NO: 6-SEQ ID NO: 1. In yet other embodiments, the transport construct is selected from the group consisting of SEQ ID NO: 1-SEQ ID NO: 3; SEQ ID NO: 1-SEQ ID NO: 4; SEQ ID NO: 1-SEQ ID NO: 5; SEQ ID NO: 1-SEQ ID NO: 6; SEQ ID NO: 3-SEQ ID NO: 1; SEQ ID NO: 4-SEQ ID NO: 1; SEQ ID NO: 5-SEQ ID NO: 1; and SEQ ID NO: 6-SEQ ID NO: 1.

The cargo moiety may be combined with or linked to the transport peptide to form the transport construct of the present invention. The transport peptide and the cargo moiety are combined or linked in such a manner that they remain combined or linked under the conditions in which the transport construct is used (e.g., under conditions in which the transport construct is administered to an individual). In certain embodiments, the cargo moiety is covalently linked to the transport peptide through a linker or a chemical bond. In other embodiments, the linker comprises a disulfide bond, or the chemical bond between the cargo moiety and the transport peptide comprises a disulfide bond. In yet other embodiments, the cargo moiety comprises a peptide moiety. In yet other embodiments, the transport peptide is covalently linked through an amide bond to the N-terminus of the peptide moiety of the cargo moiety. In yet other embodiments, the transport peptide is covalently linked through an amide bond to the C-terminus of the peptide moiety of the cargo moiety. In yet other embodiments, the transport peptide is covalently linked through an amide bond to the N-terminus and the C-terminus of the peptide moiety of the cargo moiety. Alternatively, the transport peptide and the cargo moiety are combined through a noncovalent linkage, such as electrostatic and/or hydrophobic interaction.

The invention includes functionally equivalent variants of peptides described elsewhere herein. Such variants include peptides with amino acid substitutions that maintain the functional integrity of the original peptide. Examples of amino acid substitutions include those that result in changes to the peptide wherein similar charge, polarity, hydrophobicity or structure of the original amino acid is maintained. Peptide variants also include peptide mimetics. Peptide mimetics include chemically modified peptides and peptide-like molecules containing non-naturally occurring amino acids.

In certain embodiments, the peptides of the present invention may be obtained from sources in which they occur in nature or produced using known techniques, such as chemical synthesis or genetic engineering methods (e.g., recombinant DNA or RNA technology). In other embodiments, the peptides of the invention may be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems.

In certain embodiments, isolated peptides of the present invention are relatively free from unrelated peptides, as well as contaminating polypeptides, lipids, nucleic acids and other cellular material that normally are associated with the peptide in a cell or that are associated with the peptide in a library.

The transport constructs of the invention are useful for the delivery of cargo moieties across the cell membrane. The transport constructs of the invention are also useful for the delivery of cargo moieties to a target cell (e.g., a specific cell type, such as but not limited to a cardiac cell, an endothelial cell, or an immune cell) and for the delivery of cargo moieties to a target cell and/or across the membrane of the target cell.

The transport peptides of the present invention have the ability to cross the cell membrane of a cell (e.g., internalize into the cell). For example, in certain embodiments of the invention, a transport peptide translocates from the extracellular environment of a cell, penetrates the lipid bilayer of the cell membrane, and crosses the cell membrane into the intracellular environment of the cell. In other embodiments, the transport peptides of the present invention bind to a target cell. In yet other embodiments, the transport peptides bind to and cross the cell membrane of a target cell. A target cell is a specific cell type such as, for example, a cardiac cell, an immune cell, a skin cell (e.g., an endothelial cell), a skeletal muscle cell or a brain cell (e.g. a neuron) but may be any cell, including human and nonhuman cells.

In a non-limiting example, a transport peptide of the invention is linked to a cargo moiety and transports the cargo moiety across the cell membrane of a cell. For example, In certain embodiments, a protein, such as caveolin or a transcription factor, linked to a transport peptide is carried from the extracellular environment of a cell and transported across the cell membrane and into the intracellular environment of the cell. In other embodiments, a transport peptide of the invention linked to a cargo moiety binds the cargo moiety to a target cell (e.g., a cardiac cell). In yet other embodiments, the transport peptide linked to a cargo moiety binds the cargo moiety to a target cell (e.g., a cardiac cell), and transports the cargo moiety from the extracellular environment of the target cell across the cell membrane and into the intracellular environment of the target cell.

In certain embodiments, the cargo moiety comprises an organic or inorganic compound. The organic compound may be isolated from nature (e.g., from cells in which it occurs) or may be produced using known methods, such as genetic engineering methods (e.g., recombinant DNA or RNA technology) or chemical synthetic methods. For example, an organic molecule may be an RNA molecule, polypeptide or a fragment thereof, which may be isolated from a cell, expressed from a recombinant nucleic acid molecule or synthesized chemically. An organic molecule also can be a non-naturally occurring molecule. A non-limiting example of a non-naturally occurring molecule is a nucleic acid sequence containing non-naturally occurring nucleoside analogs or phosphorothioate bonds that link the nucleotides and protect against degradation by nucleases. A ribonucleotide containing a 2-methyl group, instead of the normal hydroxyl group, bonded to the 2'-carbon atom of ribose residues, is an example of a non-naturally occurring RNA molecule that is resistant to enzymatic and chemical degradation. Other examples of non-naturally occurring organic molecules include RNA containing 2'-aminopyrimidines (wherein such RNA is 1,000 times more stable in human serum and urine as compared to naturally occurring RNA; Lin et al., 1994, Nucl. Acids Res. 22:5229-5234, and Jellinek et al., 1995, Biochemistry, 34:11363-11372).

In certain embodiments, the cargo moiety comprises a DNA, a RNA or a nucleic acid analog. The DNA or RNA may be an oligo(deoxy)nucleotide of any length. Such nucleic acid molecules may be linear, circular or super-coiled; may be single-stranded or double-stranded DNA or RNA; or may be a DNA/RNA hybrid. Nucleic acid analogs include charged and uncharged backbone analogs, such as phosphonates (e.g., methyl phosphonates), phosphoramidates (N3' or N5'), thiophosphates, uncharged morpholino-based polymers, and peptide nucleic acids (PNAs). Such molecules may be used in a variety of therapeutic regimens, including enzyme replacement therapy, gene therapy and anti-sense therapy, for example. Peptide nucleic acids (PNAs) are analogs of DNA. The backbone of a PNA is formed by peptide bonds rather than phosphate esters, making it well-suited for anti-sense applications. Since the backbone is uncharged, PNA/DNA or PNA/RNA duplexes exhibit greater than normal thermal stability. PNAs have the additional advantage that they are not recognized by nucleases or proteases. PNAs may be synthesized on an automated peptides synthesizer using standard t-Boc chemistry. The PNA may be linked to a transport peptide of the invention using known methods in the art.

In certain embodiments, the cargo moiety is a polypeptide. In other embodiments, the cargo moiety comprises caveolin or a fragment thereof. In yet other embodiments, the cargo moiety is a transcription factor or a nuclear localization peptide. In yet other embodiments, two cargo moieties, one comprising a transcription factor and the other comprising a nuclear localization peptide, are present in the transport construct of the invention.

In certain embodiments, the cargo moiety comprises a label, such as a dye or a radioactively labeled compound. In other embodiments, the cargo moiety comprises rhodamine. In yet other embodiments, the cargo moiety comprises a marker, such as green fluorescent protein, blue fluorescent protein, yellow fluorescent protein, biotin or mixtures thereof.

In a non-limiting example, recombinant techniques may be used to covalently attach a transport peptide to a cargo moiety, such as joining DNA or RNA coding for the transport peptide with DNA or RNA coding for the cargo moiety and expressing the encoded products in an appropriate host cell (a cell capable of expressing the transport construct). Alternatively, the two separate nucleotide sequences may be expressed in a cell or can be synthesized chemically and subsequently combined, using known techniques. Alternatively, the transport peptide-cargo moiety may be synthesized chemically as a single amino acid sequence and, thus, combining them is not needed.

In certain embodiments, when there is more than one cargo moiety linked to the transport peptide, the more than one moiety may be the same or different. In other embodiments, the cargo moiety or moieties are linked to the transport peptide at either the N- or C-terminus of the transport peptide. In the case wherein there are at least two cargo moieties linked to the transport peptide, one cargo moiety may be linked at the N-terminus of the transport peptide and one cargo moiety may be linked at the C-terminus of the transport peptide. Alternatively, more than one cargo moiety may be linked to either the N- or C-terminus of the transport peptide.

In certain embodiments, the cargo moiety may be linked to a transport peptide of the present invention either directly (I.e., through a chemical bond) or indirectly by means of a linker. Linkers include, for example, one or more amino acid residues. The linker may be, for example, a short sequence of 10 amino acid residues (e.g., 1 to 10, 1 to 5 or 1 to 4 amino acid residues), and may optionally include a cysteine residue through which the linker binds to the transport peptide or cargo moiety of the transport construct. A linker may also be a group such as a sulfhydryl group or carboxyl group. Suitable linkers include bi- and multi-functional alkyl, aryl, aralkyl or peptidic moieties, alkyl, aryl or aralkyl aldehydes, acids, esters and anhydrides, sulfydryl or carboxyl groups, such as maleimido benzoic acid derivatives, maleimido proprionic acid derivatives and succinimido derivatives, or may be derived from cyanuric bromide or chloride, carbonyldiimidazole, succinimidyl esters or sulfonic halides. The functional groups on the linker used to form covalent bonds between linker and cargo moiety on the one hand, as well as linker and transport peptide on the other hand, may be two or more of e.g., amino, hydrazine, hydroxyl, thiol, maleimido, carbonyl, and carboxyl groups.

In certain embodiments, the transport construct may dissociate in vitro or in vivo into the cargo moiety and transport peptide by way of chemical or enzymatic cleavage. In other embodiments, the linker comprises amino acid residues, and the in vitro or in vivo cleavage occurs within the linker.

In certain embodiments, wherein the cargo moiety is a polypeptide, the cargo moiety is linked to the transport peptide as a fusion protein by means of recombinant technology. A fusion protein is the co-linear, covalent linkage of two or more proteins via their polypeptide backbones, through genetic expression of a nucleic acid molecule encoding those proteins. The nucleic acid encoding the cargo moiety of the fusion protein is in-frame with the nucleic acid encoding the transport peptide. "In-frame" indicates that the nucleic acid sequence encoding the cargo moiety is in the correct reading frame as the nucleic acid sequence encoding the transport peptide. Therefore, the correct amino acid sequences is translated for both the transport peptide and cargo moiety of the fusion protein.

In certain embodiments, the cargo moiety is conjugated to the transport peptide via chemical cross-linking. Numerous chemical cross-linking methods are known and useful for linking the transport peptides of this invention to a cargo moiety. Coupling of the cargo moiety and the transport peptide may be accomplished via a coupling or linking agent. Intermolecular cross-linking reagents that may be utilized are exemplified in Means & Feeney, Chemical Modification of Proteins, Holden-Day, 1974, pp. 39-43, and Wong, Chemistry of Protein Conjugation and Cross-Linking, CRC Press (1991). Among these reagents are, for example, N-succinimidyl 3-(2-pyridyldithio) propionate ("SPDP") or N,N'-(1,3-phenylene) bismaleimide (both of which are highly specific for sulfydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts mainly with amino groups); glutaraldehyde (which reacts with different side chains) and disdiazobenzidine (which reacts primarily with tyrosine and histidine).

In certain embodiments, the cross-linking reagents yields a transport construct that is essentially non-cleavable under cellular conditions. In other embodiments, the cross-linking reagent contains a covalent bond, such as a disulfide, that is cleavable under cellular conditions. For example, dithiobis (succinimidylpropionate) ("DSP"), Traut's reagent and N-succinimidyl 3-(2-pyridyldithio) propionate ("SPDP") are well-known cleavable cross-linkers. The use of a cleavable cross-linking reagent permits the transport peptide to separate from the cargo moiety after delivery into the target cell. A construct comprising a direct disulfide linkage may also be useful within the methods of the invention. In certain embodiments, the cargo moiety is covalently linked to the transport peptide through a linker or a chemical bond. In other embodiments, the cross-linking reagent such as N-gamma-maleimidobutyryloxy-succinimide ester ("GMBS") and sulfo-GMBS have reduced immunogenicity.

The present invention further includes a composition comprising an isolated nucleic acid molecule that encodes the polypeptide having the fusion peptides and conservative nucleotide substitutions thereof, in certain embodiments in isolated form to generate the compositions of the invention. Conservative nucleotide substitutions include nucleotide substitutions that do not affect the coding for a particular amino acid as most amino acids have more than one codon. Conservative nucleotide substitutions thus also include silent mutations and differential codon usage.

In certain embodiments, the nucleic acid encodes a transport peptide comprising SEQ ID NO: 1. In other embodiments, the nucleic acid encodes a transport peptide consisting of SEQ ID NO: 1. In other embodiments, the nucleic acid comprises 5'-CGGCGCCCGCCTCGT-3' (SEQ ID NO: 7).

In certain embodiments, the composition further comprises a nucleic acid encoding at least one cargo moiety. In other embodiments, the cargo moiety is selected from the group consisting of a peptide; a protein; a biologically active compound; a label; an imaging agent; a diagnostic agent; a therapeutic agent; and a prophylactic agent. In yet other embodiments, the cargo moiety comprises at least one selected from the group consisting of SEQ ID NOs: 3-6. In yet other embodiments, the composition further comprises a pharmaceutically acceptable carrier.

The invention further includes an expression vector and an isolated host cell comprising nucleic acid encoding a peptide comprising SEQ ID NO: 1. In certain embodiments, the peptide consists of SEQ ID NO: 1.

The invention also includes an expression vector and an isolated host cell comprising nucleic acid encoding a cargo moiety linked to the peptide comprising SEQ ID NO: 1. In certain embodiments, the peptide consists of SEQ ID NO: 1.

In certain embodiments, the transport construct comprises a fusion protein. In other embodiments, the vector or host cell further comprises transcriptional activation elements that allow for the expression of the nucleic acid encoding the transport peptide. Expression system vectors, which incorporate the necessary regulatory elements for protein expression, as well as restriction endonuclease sites that facilitate cloning of the desired sequences into the vector, are known to those skilled in the art. In certain embodiments, the cargo moiety is in-frame with the nucleic acid encoding the transport peptide.

In a non-limiting example, a recombinant DNA expression vector containing the elements previously described is introduced into an appropriate host cell (i.e., a cell capable of expressing the transport construct) where cellular mechanisms of the host cell direct the expression of the fusion protein encoded by the recombinant DNA expression vector. Alternately, cell-free systems known to those skilled in the art may be used for expression of the fusion protein.

The purified fusion protein produced by the expression vector host cell system may then be administered to the target cell, where the transport peptide mediates the import of the fusion protein through the cell membrane of the target cell into the interior of the cell. A target cell is a specific cell type such as, for example, a cardiac cell, an immune cell, a skin cell, such as an epithelial cell; a skeletal muscle cell or a brain cell (e.g., a neuron), but may be any cell, including human and nonhuman cells.

An expression vector host cell system may be selected from among a number of such systems known to those skilled in the art. In certain embodiments, the fusion protein may be expressed in isolated host cells, such as *Escherichia coli*. In other embodiments, fusion proteins may be expressed in other bacterial expression systems, viral expression systems, eukaryotic expression systems, or cell-free expression systems. Cellular hosts used by those skilled in the art include, but are not limited to, isolated host cells such as, for example, *Bacillus subtilis*, yeast such as *Saccharomyces cerevisiae, Saccharomyces carlsbergenesis, Saccharomyces pombe*, and *Pichia pastoris*, as well as mammalian cells such as NIH3T3, HeLa, HEK293, HUVEC, rat aortic smooth muscle cells and adult human smooth muscle cells. The expression vector selected by one skilled in the art includes transcriptional activation elements such as promoter elements and other regulatory elements appropriate for the host cell or cell-free system in which the fusion protein will be expressed. In mammalian expression systems, for example, suitable expression vectors may include DNA plasmids, DNA viruses, and RNA viruses. In bacterial expression systems, suitable vectors may include plasmid DNA and bacteriophage vectors.

Examples of specific expression vector systems include the pBAD/gIII vector (Invitrogen, Carlsbad, Calif.) system for protein expression in *E. coli*, which is regulated by the transcriptional regulator AraC. An example of a vector for mammalian expression is the pcDNA3.1/V5-His-TOPO eukaryotic expression vector (Invitrogen). In this vector, the transport construct maybe expressed at high levels under the control of a strong cytomegalovirus (CMV) promoter. A C-terminal polyhistidine ($His_6$) tag enables transport construct purification using nickel-chelating resin. Secreted protein produced by this vector may be detected using an anti-His (C-term) antibody.

A baculovirus expression system may also be used for production of a transport construct comprising the transport peptide and a cargo moiety wherein the cargo moiety is a polypeptide. A commonly used baculovirus is AcMNPV. Cloning of the transport construct DNA may be accomplished by using homologous recombination. In a non-limiting example, the transport construct DNA sequence is cloned into a transfer vector containing a baculovirus promoter flanked by baculovirus DNA, particularly DNA from the polyhedrin gene. This DNA is transfected into insect cells, where homologous recombination occurs to insert the transport construct DNA into the genome of the parent virus. Recombinants are identified by altered plaque morphology.

Many transport constructs in which the cargo moiety is a peptide or protein that may not be appropriately post-translationally modified in bacterial expression systems may instead be expressed with baculovirus vectors. Enzymes, signaling molecules, mediators of cell cycle control, transcription factors, antigenic peptides, full-length protein products of viral, bacterial, or other origin for use in vaccine therapy, protein products of human cells for use in cancer vaccine therapy, toxins, and proteins involved in intracellular signaling systems that may not be appropriately post-translationally modified in bacterial expression systems may be expressed with baculovirus vectors.

Proteins as described above may also be produced by the method of the present invention by mammalian viral expression systems. An ecdysone-inducible mammalian expression system (Invitrogen, Carlsbad, Calif.) may also be used to express the transport construct wherein the transport construct is a fusion protein.

In certain embodiments, yeast host cells, such as *Pichia pastoris*, may be used for the production of a transport construct by the method of the present invention. Expression of heterologous proteins from plasmids transformed into *Pichia* has been described by U.S. Pat. No. 5,002,876 to Sreekrishna et al. Vectors for expression in *Pichia* of a fusion protein comprising a transport peptide of the present invention and a cargo moiety wherein the cargo moiety is a peptide or protein are commercially available as part of a *Pichia* Expression Kit (Invitrogen, Carlsbad, Calif.).

Purification of heterologous protein produced in *Pichia* was described by U.S. Pat. No. 5,004,688 to Craig et al., and techniques for protein purification from yeast expression systems are well known to those skilled in the art. In the *Pichia* system, commercially available vectors may be selected from among those that are more suited for the production of cytosolic, non-glycosylated proteins and those that are more suited for the production of secreted, glycosylated proteins, or those directed to an intracellular organelle, so that appropriate protein expression may be optimized for the cargo moiety of choice that is a polypeptide.

Methods

The invention includes a method of delivering a cargo moiety to or into, also referred to as (in)to, a target cell. In certain embodiments, the method comprises contacting the target cell with a transport construct, wherein the transport construct comprises a cargo moiety and a transport peptide comprising SEQ ID NO: 1, whereby the cargo moiety is delivered (in)to the target cell.

The invention further includes a method of delivering a cargo moiety (in)to a target cell of a subject in need thereof. In certain embodiments, the method comprises administering to the subject a therapeutically effective amount of a pharmaceutically acceptable composition comprising a transport construct, wherein the transport construct comprises the cargo moiety and a transport peptide comprising SEQ ID NO: 1, whereby the cargo moiety is delivered (in)to the target cell of the subject.

In certain embodiments, the cargo moiety is covalently linked to the transport peptide through a linker or a chemical bond. In other embodiments, the linker comprises a disulfide bond, or the chemical bond between the cargo moiety and the transport peptide comprises a disulfide bond. In yet other embodiments, the cargo moiety comprises a peptide moiety. In yet other embodiments, the transport peptide is covalently linked through an amide bond to the N-terminus of the peptide moiety of the cargo moiety. In yet other embodiments, the transport peptide is covalently linked through an amide bond to the C-terminus of the peptide moiety of the cargo moiety. In yet other embodiments, the transport peptide is covalently linked through an amide bond to the N-terminus and the C-terminus of the peptide moiety of the cargo moiety.

In certain embodiments, the transport peptide consists of SEQ ID NO: 1. In other embodiments, the cargo moiety is at least one selected from the group consisting of a nucleic acid; a peptide; a protein; an oligosaccharide; a lipid; a glycolipid; a lipoprotein; a small molecule compound; a therapeutic drug; an UV-vis, fluorescent or radioactive label; an imaging agent; a diagnostic agent; a prophylactic agent; a liposome and a virus. In yet other embodiments, the target cell comprises an endothelial cell, a cardiac cell, an immune cell, a skeletal muscle cell or a brain cell. In yet other embodiments, a composition of the invention is administered to the subject by at least one route selected from the group consisting of oral, transmucosal, topical, transdermal, intradermal, subcutaneous, ophthalmic, intravitreal, subconjunctival, suprachoroidal, intracameral, inhalational, intrabronchial, pulmonary, intravenous, intra-arterial, intraduodenal, intravesical, parenteral, intrathecal, intramuscular and intragastrical. In yet other embodiments, the subject is a mammal. In yet other embodiments, the mammal is human.

Combination Therapies

The compositions useful within the present invention are intended to be useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, in certain embodiments a mammal, in other embodiments a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions useful within the invention are formulated using one or more pharmaceutically acceptable excipients or carriers. In certain embodiments, the pharmaceutical compositions of the invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, and thimerosal. In many cases, isotonic agents, for example, sugars, sodium chloride, or polyalcohols such as mannitol and sorbitol, can be included in the composition. Prolonged absorption of the injectable compositions may be brought about by including in the composition an agent which delays absorption, for example, aluminum monostearate or gelatin.

In certain embodiments, the compositions useful within the invention are administered to the patient in dosages that range from one to five times per day or more. In other embodiments, the compositions useful within the invention are administered to the patient in range of dosages that include, but are not limited to, once every day, every two, days, every three days to once a week, and once every two weeks. It will be readily apparent to one skilled in the art that the frequency of administration of the various combination compositions useful within the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In certain embodiments, the dose of a compound is from about 1 mg and about 2,500 mg. In other embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other cognition improving agents.

The term "container" includes any receptacle for holding the pharmaceutical composition. For example, In certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of administration of any of the compositions of the invention include oral, buccal, topical, transdermal, intradermal, subcutaneous, transmucosal [e.g., sublingual, lingual, (trans)buccal, (trans)urethral, vaginal (e.g., trans- and perivaginally), (intra)nasal and (trans)rectal], ophthalmic (e.g., intravitreal, subconjunctival, suprachoroidal, intracameral), inhalational, intrabronchial, pulmonary, intraduodenal, intravenous, intra-arterial, intravesical, parenteral, intrathecal, intramuscular or intragastrical route. The compounds for use in the invention may be formulated for administration by any suitable route considered herein.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, the compounds may be formulated for injection or infusion, for example, intravenous, intramuscular or subcutaneous injection or infusion, or for administration in a bolus dose and/or continuous infusion. Solutions, suspensions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation. In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 min up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 min, about 20 min, or about 10 min and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 min, about 20 min, or about 10 min, and any and all whole or partial increments thereof after drug administration.

Dosing

The therapeutically effective amount or dose of a compound will depend on the age, sex and weight of the patient, the current medical condition of the patient and the progression of Parkinson's Disease in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Cell Isolation and Culture:

Cultured rat heart microvascular endothelial cells (RHM-VEC) were purchased from VEC Technologies (Rensselaer, N.Y.) and grown on fibronectin coated plates in MCDB-131 complete medium (VEC Technologies). BAEC were isolated from bovine aortas obtained from a local slaughter house and grown in DMEM (high glucose; Cellgro) supplemented with 10% FBS (Hyclone) and pen/strep. HUVECS were isolated locally from human umbilical cords and grown in M199 medium (Invitrogen) supplemented with endothelial cell growth supplement (Invitrogen), 10% FBS, L-glutamine (Invitrogen) and pen/strep.

T7 PhageLibrary Construction:

Novagen T7select phage display system was used for the random screening of peptides that facilitate endothelial cell uptake in conjunction with a pool of oligonucleotides randomly coding for 7-mer peptides. The 7-mer random peptide primers containing HindIII/XhoI sites were designed as follows: Sense primer: 5'-GCTAGAATTCNNNBNNBNN-BNNBNNBNNBNNBAAGCTTACTGCAGTAGCATG-3' (SEQ ID NO: 9); Anti-sense primer 5'-CATGCTACTGCA-GTAAGCTT-3' (SEQ ID NO: 10); wherein N=A, T, C, G; and B=G, C, T.

Similar amount of each primer were mixed and annealed at 95° C. for 5 min, then cooled down to room temperature. Fill-in reactions were then performed by using the Klenow enzyme to generate blunt ends DNA fragments. After HindIII/XhoI digestion, 0.06 pmol of inserts were ligated into T7select415-lb vector. The ligation reaction was added directly to T7 packaging Extracts for in vitro packaging, and a $3\times10^7$ pfu of phage library was generated. For amplification, the library was inoculated with BL21 culture ($OD_{600}$ of 0.5-1.0) and induced with 1 mM IPTG at 37° C. for 2 hours until cell lysis was observed. The lysate containing phages was clarified by centrifugation at 8000×g for 10 min, the supernatant was titered and aliquots were stored a 4° C.

Phage Selection by Endocytosis in EC and Amplification:

RHMVEC (80% confluent; approximately $2\times10^7$ cells/100 mm dish) were washed with PBS and pre-incubated in serum-free medium at 37° C. for 30 min and inoculated with an extract ($5\times10^9$ pfu) of the T7 phage library to reach a multiplicity of infection (MOI) of 250. After incubation for 1 hour at 37° C., cells were washed with ice-cold PBS and acid washed with 0.1N HCl, pH 2.2, for 15 seconds to remove unbounded and weakly associated phages from the cell surface. Cells were then trypsinized, centrifuged and lysed with sterile deionized water on ice. Cell debris were removed by centrifugation and the supernatant containing previously internalized phages were amplified as described above and titered between each round to ensure that $5\times10^9$ pfu of input phages was used at the start of each successive round. After completion of six rounds of selection/amplification, *Eshcherichia Coli* BL21 was infected with the resulting phages and plated, individual plaques were picked, amplified and sequenced.

Peptide Synthesis:

Peptides, corresponding to Endo5 (RRPPR) (SEQ ID NO: 1) or *Antennapedia* (RQIKIWFQNRRMKWKK) (SEQ ID NO: 2) with or without cargo fused to their C-terminus end (caveolin-1 amino acids 82-101; DGIWKASFTTFTVTKY-WFYR) (SEQ ID NO: 5) were synthesized by standard Fmoc chemistry and analyzed by mass spectrometry to confirm purity by the W.M. Keck biotechnology resource center at Yale University School of Medicine. Fluorophores (carboxyfluorescein for Endo5 and rhodamine for AP) were added to the N-terminus following synthesis.

Before each experiment, desiccated peptides were weighed, dissolved in dimethyl sulfoxide (DMSO; J. T. Baker, Philipsburg, N.J.) to $5\times10^{-2}$-$10^{-2}$ M and diluted to $10^{-3}$ M with distilled water.

NO Release:

VEGF-induced NO release experiments were performed as previously described.

Briefly, confluent BAEC were incubated in serum-free DMEM for 6 hours with peptides. Media was removed and fresh serum-free DMEM was added, with or without VEGF ($10^{-9}$ M) for 30 min. Media was collected, cells were trypsinized and counted, and nitrites levels in the supernatant were determined by using a Sievers NO chemiluminescence analyzer.

Modified Miles Assay:

Plasma leakage in mouse skin was studied using the Miles assay as previously described. Briefly, male swiss mice (30-35 g) were anesthetized and injected with Evans blue (30 mg/kg in PBS; Sigma). Phenylisothiocyanate (5% in mineral oil), an analog of mustard oil (Pierce, Rockford, Ill.) was applied on the right ear with a cotton tip. The left ear was used as a control and was treated with mineral oil alone. After 30 min, the anesthetized animals were sacrificed, perfused, ears were removed, dried and weighed. Evans blue was extracted from the ears with formamide and quantified spectrophotometrically at 595 nm.

Quantification of Internalization:

Cultured BAEC were grown in 6-well plates until confluency was reached. Cells were washed and incubated in 1 mL of DMEM containing labeled peptides ($10^{-6}$ M) for 1, 2, 4 or 6 hours at 37° C., washed three times with cold PBS containing 0.1 M glycine (pH 4) to remove non-specific surface staining. After complete media removal, cells were trypsinized, centrifuged and proteins were extracted by adding 150 μL of SDS-based or Triton X-100 lysis buffer. Membranes were removed by centrifugation, and internalized peptides were quantified by using a fluorescence plate reader (Perseptive Biosystems). Cells incubated with peptides for 5 min and washed as described were used as basal surface staining. Linearity of both fluorophores used was determined by performing a concentration-fluorescence curve using lysis solution. Experiments with each fluorophore were performed individually to prevent cross-interference.

CPP Imaging in Live HUVEC:

Freshly isolated HUVEC were grown in M199 media supplemented with glutamine, 10% FBS and endothelial cell growth supplement on Petri dishes with glass bottom. Since CPPs bind non-specifically to glass, the background fluorescence was reduced by pretreating glass-bottom Petri dishes with a blocking solution containing unlabelled AP and Endo5 for 30 min ($5\times10^{-5}$ M) in colorless M199 media with 1% FBS. After cell seeding, media was removed and carboxyfluorescin-labeled Endo5 and Rhodamine-labeled AP were added to cells ($10^{-5}$ M) and cells were incubated at 37° C. and 5% $CO_2$ for 1 hour (pulse). Media was removed, cells were rinsed once with warm culture media and peptide uptake was rapidly visualized on a Zess Axiovert inverted fluorescence microscope by performing a Z-stack of captured images followed by volume deconvolution (Openlab software). The new media was left on cells for an additional 2 hours (total 3 hours) to chase CPP localization, and cells were visualized again (chase).

Statistical Analysis:

Data are mean±S.E. Statistical comparisons were made by analysis of variance followed by an unpaired Student's t test. Data were considered significantly different if values of $p<0.05$ were observed.

Example 1: Screening of Phage Library for Peptides that Mediate Phage Internalization A T7 phage display library that expresses on average 0.1-1 copy of randomly generated 7-mer peptides on the capsid was generated. This system was used because the low peptide number on the capsid makes it suitable for the selection of peptides that bind strongly to their targets. A constant amount of input phages ($5\times10^9$) was added to cultured RHMVEC and these phages were selected for their capacity to get quickly internalized (cellular uptake) by the cell monolayer. After six rounds of infection/purification, a 100-fold increase in the percentage of recovered phages was observed, from 0.018 (round 1) to 1.8% (round 6) under identical starting conditions (Table 1), providing evidence that the resulting phage library displays enhanced endothelial cell internalization properties. Analysis of the phage library's capacity of internalization in endothelial cells after each round of selection suggests an exponential increase in the uptake percentage (FIG. 1, $R^2$=0.975 for correlation with exponential function).

Following completion of biopanning and enrichment, the resulting phages were plated, and individual plaques were amplified and sequenced. Out of the 24 individual phages isolated, five phages were coding for the unexpectedly short 5-mer peptide RRPPR (SEQ ID NO: 1), termed Endo5, which was the most frequently identified peptide (21%). Codon analysis of the DNA sequence of Endo5 coding phage revealed the random and unexpected insertion of a stop codon in the coding sequence (CGGCGCCCGC-CTCGTTGAGGG) (SEQ ID NO: 8), which rationalized the smaller size of Endo5 compared to the theoretical CPP size our approach can generate (7 amino acids).

Without wishing to be limited by any theory, the high recovery of Endo5 after phage biopanning may be attributable to its relatively small size compared to theoretical 7-mer peptides for which the biopanning approach is designed. However, other CPP ranging from 4 to 7 amino acids were isolated with the technique described herein, and none of them display the high recovery rate of Endo5, arguing against a size-dependent selection.

Example 2: eNOS Inhibitory Activity

AP-Cav blocks agonist-induced eNOS activity in cultured endothelial cells (Bucci et al., 2000, Nat. Med. 6:1362-7), and this biological activity is dependent on AP-Cav's internalization, dosage and pretreatment time. In the present study, the uptake potential of Endo5 was compared with that of AP by testing the effect of Endo5 fused to Cav (endo5-Cav) on NO release by cultured BAEC.

Figure 2A:
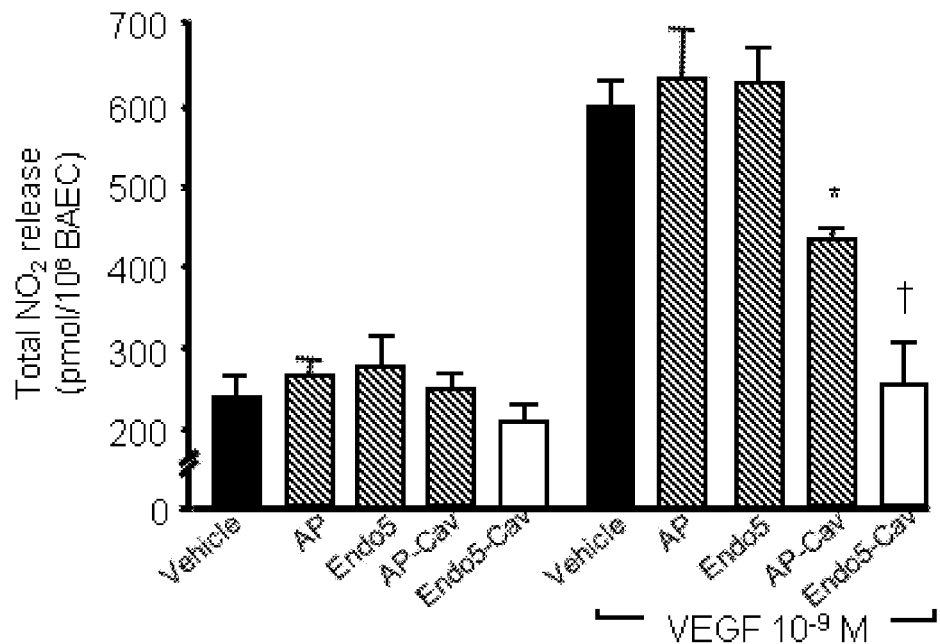
FIGS. 2A-2D are a series of bar graphs illustrating the finding that Endo5-Cav is more potent than AP-Cav at blocking VEGF-induced NO release.

A six-hour pretreatment of BAEC with AP or Endo5 without cargo, or with AP-Cav or Endo5-Cav ($10^{-5}$ M) had no significant effect on basal (unstimulated) NO release (FIG. 2A) as assayed by NO-specific chemiluminescence. Similar pretreatment with AP or Endo5 showed no significant effect on VEGF-induced NO release, whereas pretreatment with AP-Cav ($10^{-5}$M) blocked VEGF activity by 48% (Bucci et al., 2000, Nat. Med. 6:1362-7). Interestingly, similar pretreatment with Endo5-Cav ($10^{-5}$ M) completely impaired VEGF activity on BAEC NO release (FIG. 2A), providing evidence that Endo5-mediated uptake was more efficient than that of AP.

Figure 2B:
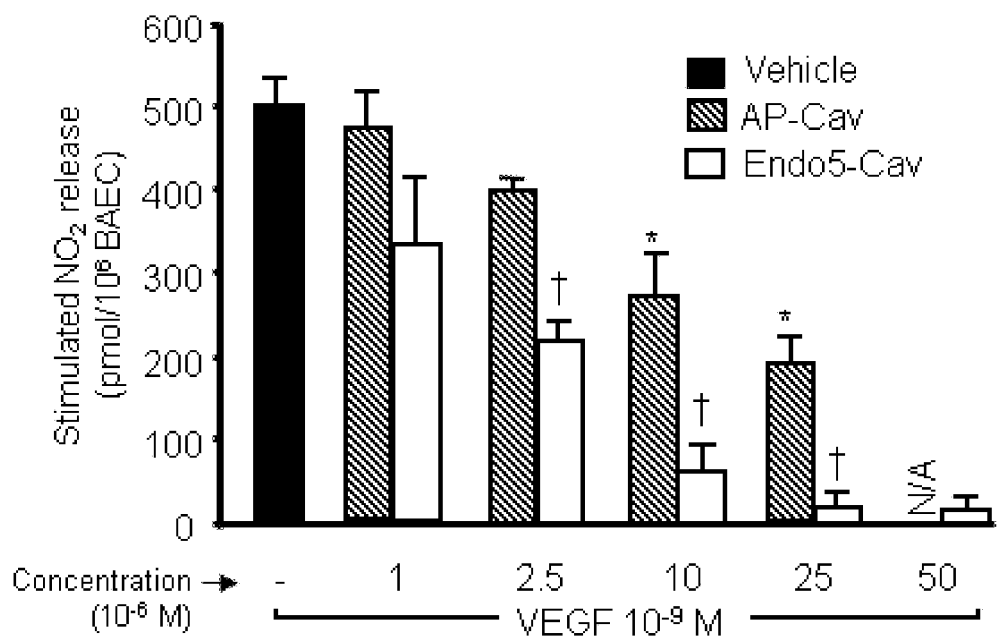

The pharmacological effect of Endo5-Cav on VEGF-induced NO release was further studied by performing dose-dependent inhibition experiments. Pretreatment with Endo5-Cav ($10^{-6}$-$10^{-5}$ M) caused a dose-dependent inhibition of VEGF-induced NO release (FIG. 2B) with a near-maximum effect at $10^{-5}$ M. AP-Cav activity reached maximum inhibition at $2.5 \times 10^{-5}$M due to peptide insolubility at greater dose but displayed a much weaker inhibitory activity (61% inhibition). Analysis of dose response curves followed by non-linear regression (curve fit) revealed that the $EC_{50}$ of AP-Cav and Endo5-Cav were $1.8 \times 10^{-6}$ and $7.5 \times 10^{-6}$ M, respectively.

Since the inhibition of Endo5-Cav on VEGF-induced eNOS activity was more robust than that of AP-Cav at a similar concentration, a time-dependent comparison between AP-Cav and Endo5-Cav effect on eNOS activity was performed. AP-Cav ($10^{-5}$ M) had a time-dependent effect on VEGF-induced NO release in BAEC (FIG. 2C) although a minor difference is observed between 4 h and 6 h incubation time points (57% vs 49%, respectively), suggesting that a near-complete equilibrium between AP-Cav uptake and intracellular degradation/elimination may be reached.

Figure 2C:
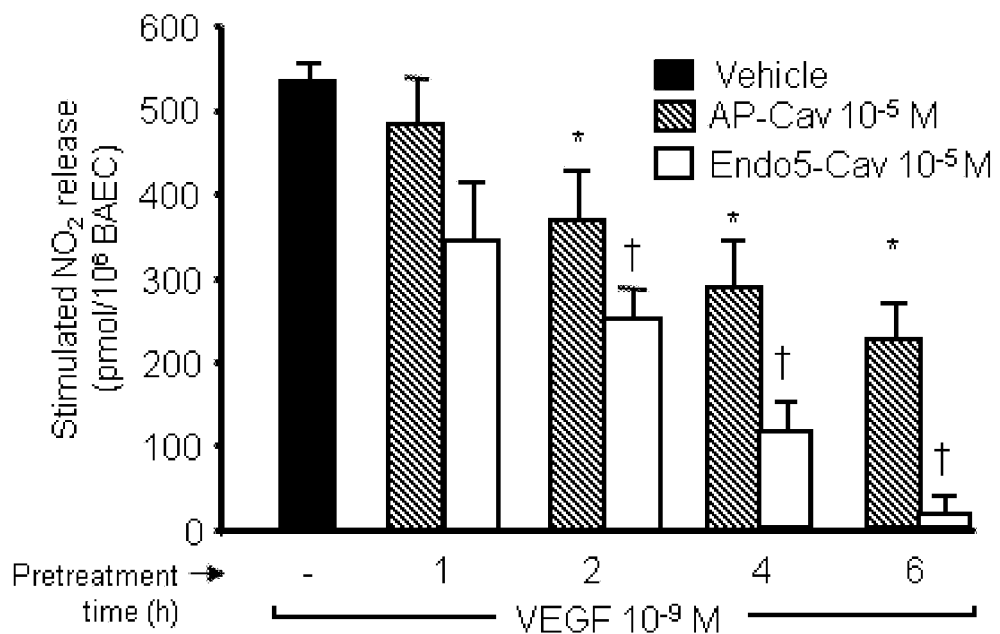

Endo5-Cav inhibitory effect was also time-dependent but more robust, with a complete eNOS inhibition at 4 hours, suggesting a faster internalization of Endo5. Moreover, the data indicated that a six-hour pretreatment with AP-Cav ($10^{-5}$ M) had a similar effect on VEGF-induced NO release as compared to a two-hour pretreatment with Endo5-Cav at a similar concentration, which provided evidence that the rate of uptake Endo5-Cav was approximately three times that of AP-Cav (FIG. 2C).

Figure 2D:
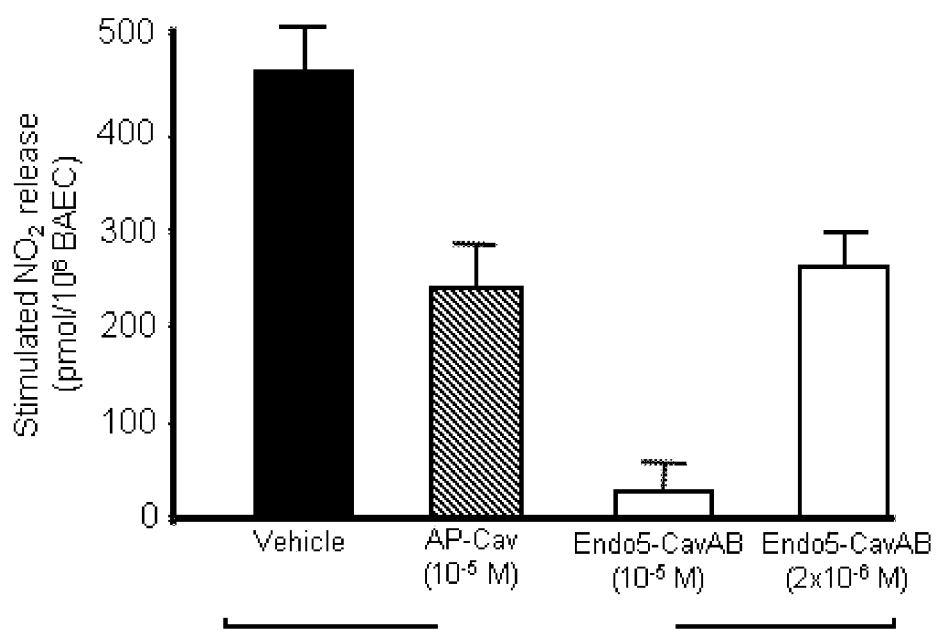

The Cav AB domain (amino acids 82-95; SEQ ID NO: 6) mediates eNOS inhibition (Bernatchez et al., 2005, Proc. Natl. Acad. Sci. 102:761-66). Because Endo5 appears more potent that AP at promoting cargo internalization, both AP-Cav leader and cargo sequences were modified in order to maximize the therapeutic effect/size ratio compared to AP-Cav. Hence, Endo5-CavAB (a 19-mer peptide) was synthesized and its activity was compared to that of AP-Cav (a 36-mer acid peptide). Pretreatment of BAEC for six hours with Endo5-CavAB ($10^{-5}$ M) completely blocked VEGF-induced NO release, whereas AP-Cav inhibited VEGF effect by only 52% (FIG. 2D) at a similar dose. Interestingly, pretreatment with Endo5-CavAB ($2 \times 10^{-6}$ M) had a similar effect as AP-Cav ($10^{-5}$ M), inhibiting VEGF-induced NO release by 49%.

Taken together, these data suggest the feasibility of optimizing both AP-Cav cell uptake sequence and cargo to maximize the therapeutic potential per molecule or per amino acid.

Example 3: Anti-Inflammatory Properties

EC-derived NO production plays an active role in inflammation, in part by promoting increase in intra-capillary pressure and subsequent vascular permeability. Pretreatment of mice with AP-Cav blocks vascular leakage in the Miles assay (Bucci et al., 2000, Nat. Med. 6:1362-7; Bernatchez et al., 2005, Proc. Natl. Acad. Sci. USA 102:761-6). This established model may thus be a valuable tool to asses the in vivo potency of Endo5-fused peptides.

Figure 3A:
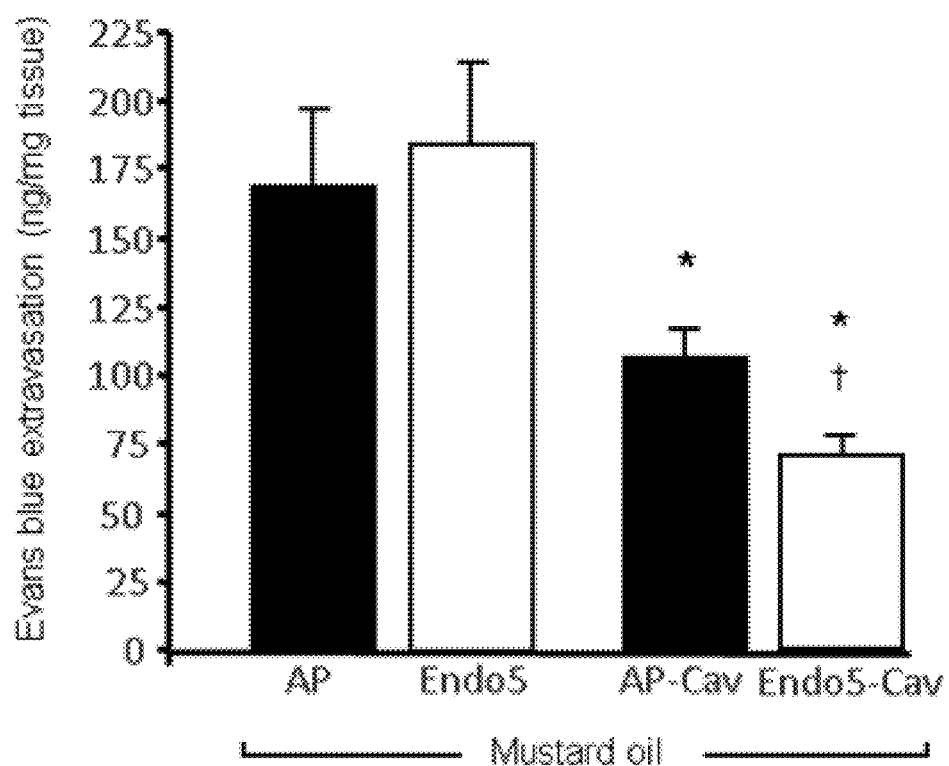
FIGS. 3A-3B illustrate the finding that Endo5-Cav blocks Evans blue extravasation in vivo.
Figure 3B:
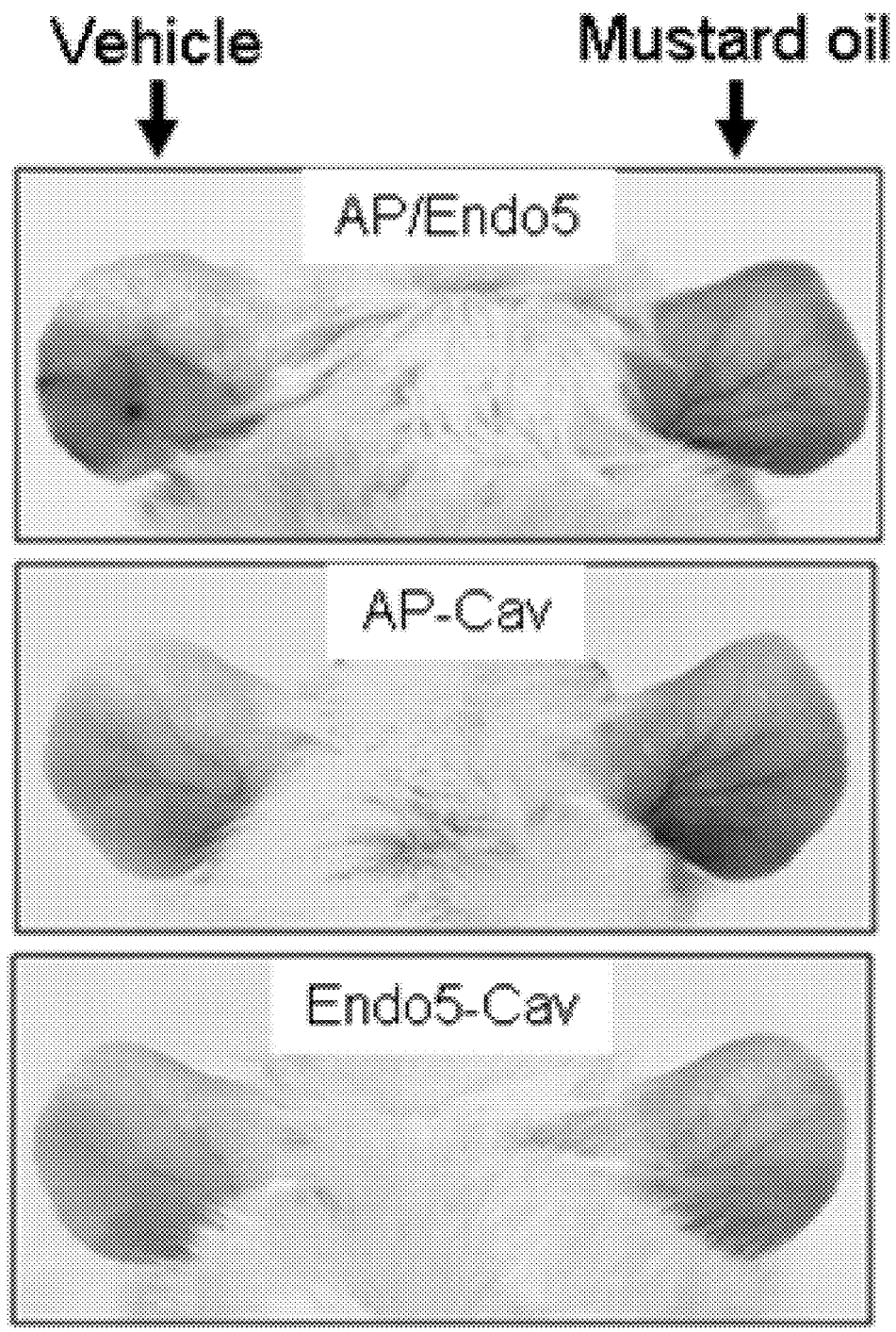

An one-hour pretreatment of mice with AP-Cav (1 mg/kg) (FIG. 3A) attenuated by 37% (n=6 per group) compared to mice treated with AP alone (similar dose on a molecular weight basis). Endo5-Cav inhibited mustard oil-induced vascular leakage by 58% compared with Endo5 pretreatment alone (n=6 or 8 per group) and showed a statistically significant greater inhibitory activity than AP-Cav (†P<0.05). As illustrated in FIG. 3B, both AP-Cav and Endo5-Cav attenuate Evans blue extravasation in the ear skin and tissue compared to control peptides, although Endo5-Cav was more potent. Without wishing to be limited by any theory, the incomplete inhibition displayed by Endo5-Cav on mustard oil-induced inflammation may be explained by the observation that NO plays only a partial role in mediating vascular permeability in this model (Bucci et al., 2000, Nat. Med. 6:1362-7).

Example 4: Internalization by Endothelial Cells

AP is a CPP that crosses the membrane of neurons (Joliot et al., 1991, Proc. Natl. Acad. Sci. USA 88:1864-8). As discussed elsewhere herein, Endo5 was unexpectedly found to promote high internalization of phages in endothelial cells, and Endo5-Cav was unexpectedly found to be more potent that AP-Cav at preventing eNOS activation and vascular permeability.

Figure 4A:
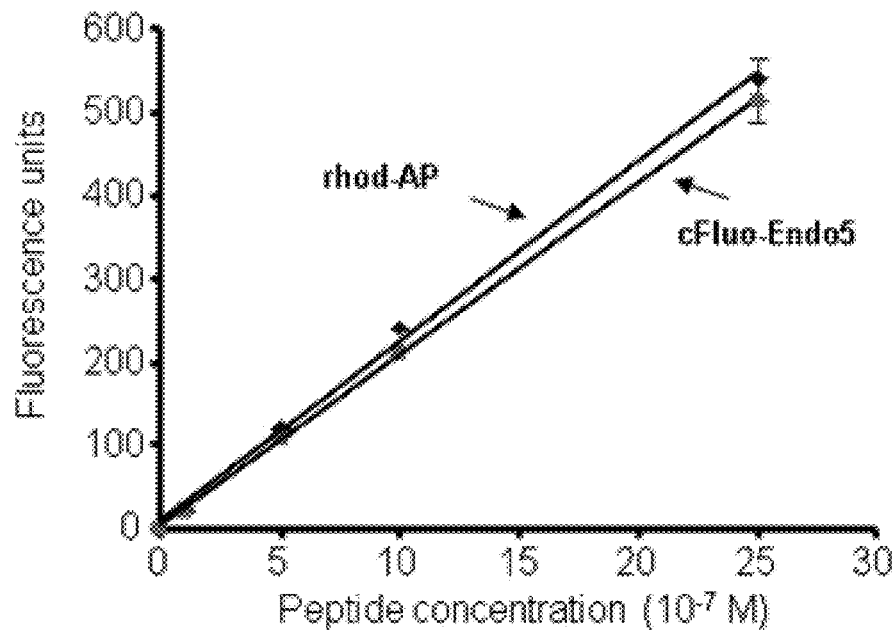
FIGS. 4A-4B are a series of graphs illustrating the finding that Endo5 is internalized faster than AP in cultured endothelial cells.

In the present study, the internalization rate of Endo5 was directly compared to that of AP by using carboxyfluorescein and rhodamine-labelled form of each peptide, respectively. The linearity of each fluorophore-coupled peptide was confirmed by performing a standard concentration/fluorescence curve. As illustrated in FIG. 4A, calibration was performed in order to obtain similar absorbance values for both fluorophores (by adjusting gain settings for each fluorophores). BAEC were incubated separately with fluorophore-labelled peptides ($10^{-6}$ M) for 1, 2, 4 or 6 hours, acid washed, lysed, and total peptide uptake was determined by quantifying fluorescence.

Figure 4B:
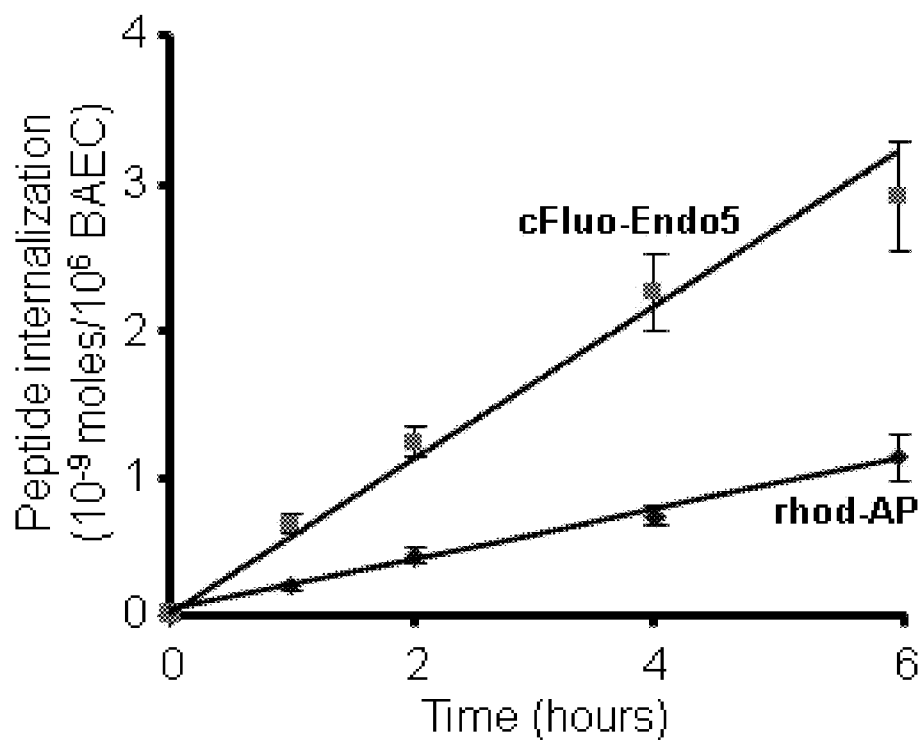

A linear increase in AP internalization with time was observed (FIG. 4B), peaking at 6 hours at a value of $1.07 \times 10^{-9}$ moles of AP/$10^6$ cells. This indicates that approximately 11% of the total amount of rhodamine-AP added at time zero is internalized by a confluent BAEC monolayer in the settings, providing evidence for an active concentration mechanism. The rate of internalization of carboxyfluorescein-Endo5 was greater than that of AP, also peaking at 6 hours with a value of $2.85 \times 10^{-9}$ moles of Endo5/$10^6$ cells, suggesting that 30.5% of the added peptide was internalized after 6 hours (FIG. 4B).

Example 5: Internalization in Live Endothelial Cells

In prior studies that attempted to shed light on the uptake mechanisms involved in CPP entry into cells, imaging was performed in fixed cells. The results of these studies may not be reliable in view of the mounting evidence that cell fixation leads to the unexpected nuclear translocation of CPP (Richard et al., 2003, J. Biol. Chem. 278:585-90).

Figure 5A:
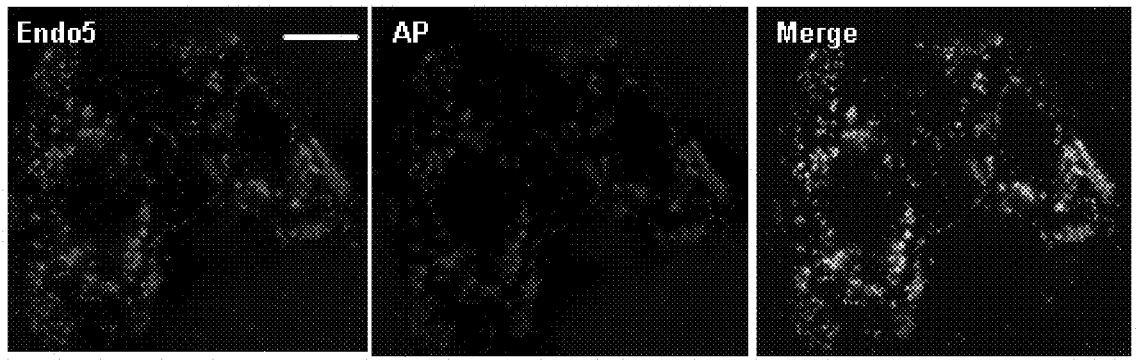
FIGS. 5A-5C illustrate the finding that internalization of Endo5 and AP uses overlapping cellular pathways in endothelial cells.

In the present study, epifluorescence microscopy experiments were performed in live HUVEC to compare the uptake mechanism of Endo5 to AP. After blocking glass bottom Petri dishes with unlabelled AP and Endo5 to minimize non-specific binding of labeled peptides, freshly isolated HUVEC were grown to 50% confluent and labeled with a "pulse" of carboxyfluorescein-Endo5 and rhodamine-AP ($10^{-6}$M) for 1 h, rinsed, followed by a two-hour "chase" for a total of 3 hours. Deconvoluted images were captured after the "pulse" and "chase" periods. Both Endo5 (green channel) and AP (red channel) display diffuse punctate cytoplasmic staining in live HUVEC after 1 h of incubation at 37° C. (FIG. 5A). Nuclear staining was nearly completely absent (dark central area). Interestingly, merged images revealed a high degree of co-localization between Endo5 and AP, characterized by the yellow color (FIG. 5A, left). This observation suggests similarity between Endo5 and AP early internalization pathways. Individual incubation of HUVEC with rhodamine-AP caused little or no signal in the carboxyfluorescein-Endo5 channel and vice-versa, suggesting the absence of significant bleed-through.

Figure 5B:
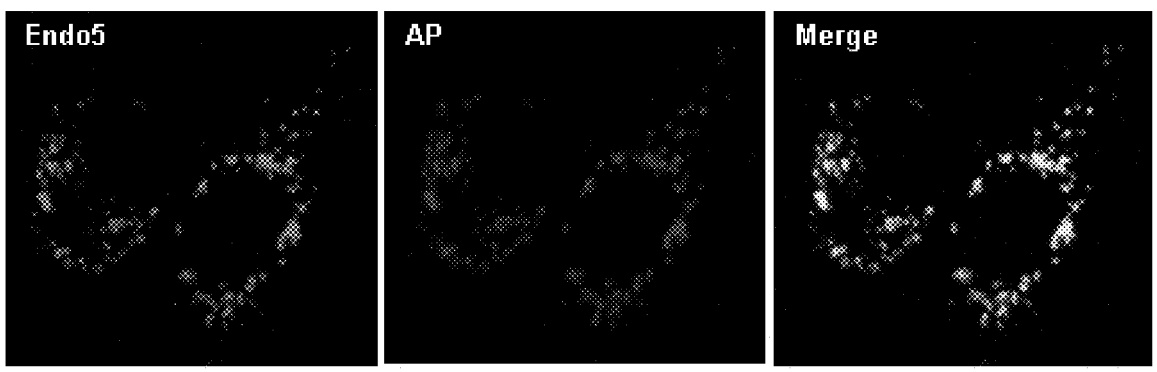

After a two-hour "chase" period in absence of CPP, the punctate staining for both Endo5 and AP was still noticeable but it displayed a more concentrated rather than diffuse pattern, stressing an active intracellular concentration/localization mechanism (FIG. 5B, left). Merged images again revealed colocalization between Endo5 and AP during this long-term phase of intracellular peptide concentration (chase) after initial internalization from the cell surface. Representative cells were shown. Taken together, these data illustrated the similarity of the internalization and intracellular distribution between Endo5 and AP.

Figure 5C:
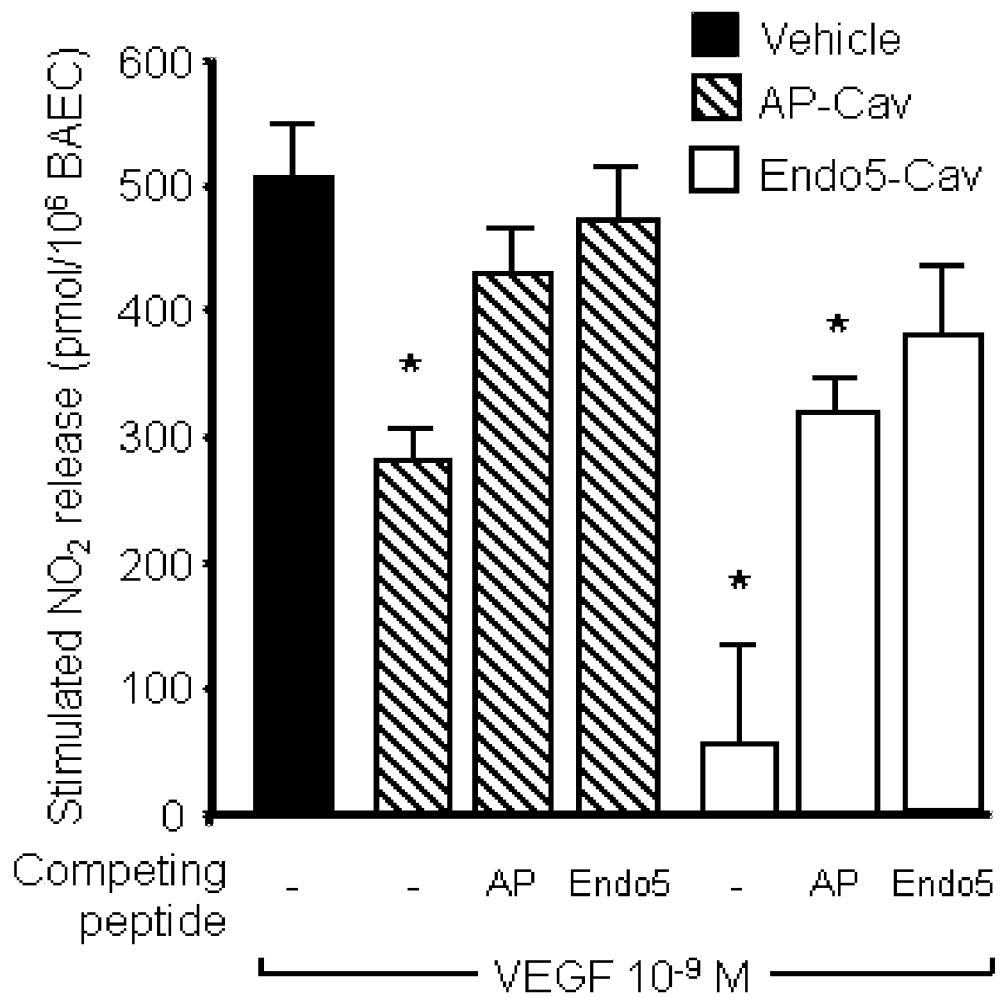

The similarity of the internalization pathways between Endo5 and AP was confirmed by performing competition studies and quantifying Endo5 and AP ability to promote cargo entry into cells. As illustrated in FIG. 5C, AP-Cav ($10^{-5}$M) partial effect on VEGF-induced NO release was blocked by pretreatment with either AP or Endo5 ($5 \times 10^{-5}$ M). The near-complete inhibition of VEGF-induced NO release mediated by Endo5-Cav was partially prevented by pretreatment with either AP or Endo5 ($5 \times 10^{-5}$ M). As illustrated in FIG. 5C, the 91% inhibition of VEGF-induced NO release by Endo5-Cav was prevented by AP (30% inhibition) or Endo5 (13% inhibition). Taken together, these results suggest that AP and Endo5 are internalized through similar pathways in EC.

TABLE 1

Enrichment of phage internalization capacity following 6 rounds of biopanning
RHMVEC were incubated for 1 hour with $5.0 \times 10^9$ phages (input), lysed, and recovered phages were quantified (cell uptake) and amplified for the next round of biopanning. Recovery percentage is expressed as the ratio of recovered phages to input phages.

| Round of infection | Input phages (supernatant) | Recovered phages (cell uptake) | Recovery % |
|---|---|---|---|
| 1 | $5.0 \times 10^9$ | $9.4 \times 10^5$ | 0.018 |
| 2 | $5.0 \times 10^9$ | $3.8 \times 10^6$ | 0.076 |
| 3 | $5.0 \times 10^9$ | $7.5 \times 10^6$ | 0.15 |
| 4 | $5.0 \times 10^9$ | $2.8 \times 10^7$ | 0.56 |
| 5 | $5.0 \times 10^9$ | $4.5 \times 10^7$ | 0.90 |
| 6 | $5.0 \times 10^9$ | $9.0 \times 10^7$ | 1.8 |
|  |  |  | 24 individual phages isolated |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated construct, or a salt or solvate thereof, comprising a peptide having at least 90% sequence homology to an amino acid sequence selected from the group consisting of SEQ ID NOs: 3-6, wherein the peptide further comprises a transport peptide comprising the amino acid sequence RRPPR (SEQ ID NO: 1).

2. The construct of claim 1, formulated in a pharmaceutical composition comprising a pharmaceutically acceptable carrier.

3. The construct of claim 1, wherein the peptide having at least 90% sequence homology is selected from the group consisting of SEQ ID NOs: 5-6.

4. The construct of claim 3, formulated in a pharmaceutical composition comprising a pharmaceutically acceptable carrier.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Chemically Synthesized

<400> SEQUENCE: 1

Arg Arg Pro Pro Arg
1               5

<210> SEQ ID NO 2
<211> LENGTH: 16
<212> TYPE: PRT
<213> ORGANISM: Artificial Sequence
<220> FEATURE:
<223> OTHER INFORMATION: Chemically Synthesized
```

<400> SEQUENCE: 2

Arg Gln Ile Lys Ile Trp Phe Gln Asn Arg Met Lys Trp Lys Lys
1               5                   10                  15

<210> SEQ ID NO 3
<211> LENGTH: 178
<212> TYPE: PRT
<213> ORGANISM: Homo sapiens

<400> SEQUENCE: 3

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Val Val
    50                  55                  60

Lys Ile Asp Phe Glu Asp Val Ile Ala Glu Pro Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Ile
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 4
<211> LENGTH: 151
<212> TYPE: PRT
<213> ORGANISM: Homo sapiens

<400> SEQUENCE: 4

Met Met Ala Glu Glu His Thr Asp Leu Glu Ala Gln Ile Val Lys Asp
1               5                   10                  15

Ile His Cys Lys Glu Ile Asp Leu Val Asn Arg Asp Pro Lys Asn Ile
            20                  25                  30

Asn Glu Asp Ile Val Lys Val Asp Phe Glu Asp Val Ile Ala Glu Pro
        35                  40                  45

Val Gly Thr Tyr Ser Phe Asp Gly Val Trp Lys Val Ser Tyr Thr Thr
    50                  55                  60

Phe Thr Val Ser Lys Tyr Trp Cys Tyr Arg Leu Leu Ser Thr Leu Leu
65                  70                  75                  80

Gly Val Pro Leu Ala Leu Leu Trp Gly Phe Leu Phe Ala Cys Ile Ser
                85                  90                  95

Phe Cys His Ile Trp Ala Val Val Pro Cys Ile Lys Ser Tyr Leu Ile
            100                 105                 110

Glu Ile Gln Cys Ile Ser His Ile Tyr Ser Leu Cys Ile Arg Thr Phe
        115                 120                 125

Cys Asn Pro Leu Phe Ala Ala Leu Gly Gln Val Cys Ser Ser Ile Lys
            130                 135                 140

Val Val Leu Arg Lys Glu Val
145                 150

<210> SEQ ID NO 5
<211> LENGTH: 20
<212> TYPE: PRT
<213> ORGANISM: Homo sapiens

<400> SEQUENCE: 5

Asp Gly Ile Trp Lys Ala Ser Phe Thr Thr Phe Thr Val Thr Lys Tyr
1               5                   10                  15

Trp Phe Tyr Arg
            20

<210> SEQ ID NO 6
<211> LENGTH: 14
<212> TYPE: PRT
<213> ORGANISM: Homo sapiens

<400> SEQUENCE: 6

Asp Gly Ile Trp Lys Ala Ser Phe Thr Thr Phe Thr Val Thr
1               5                   10

<210> SEQ ID NO 7
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 7
cggcgcccgc ctcgt                                                    15

<210> SEQ ID NO 8
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 8
cggcgcccgc ctcgttgagg g                                             21

<210> SEQ ID NO 9
<211> LENGTH: 52
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (11)..(11)
<223> OTHER INFORMATION: A, T, C, or G
<220> FEATURE:
<221> NAME/KEY: misc_feature
<222> LOCATION: (12)..(12)
<223> OTHER INFORMATION: A, T, C, or G
<220> FEATURE:
<221> NAME/KEY: misc_feature
<222> LOCATION: (13)..(13)
<223> OTHER INFORMATION: A, T, C, or G
<220> FEATURE:
<221> NAME/KEY: misc_feature
<222> LOCATION: (14)..(14)
<223> OTHER INFORMATION: G, C, or T -continued

```
<220> FEATURE:
<221> NAME/KEY: misc_feature
<222> LOCATION: (15)..(15)
<223> OTHER INFORMATION: A, T, C, or G
<220> FEATURE:
<221> NAME/KEY: misc_feature
<222> LOCATION: (16)..(16)
<223> OTHER INFORMATION: A, T, C, or G
<220> FEATURE:
<221> NAME/KEY: misc_feature
<222> LOCATION: (17)..(17)
<223> OTHER INFORMATION: G, C, or T
<220> FEATURE:
<221> NAME/KEY: misc_feature
<222> LOCATION: (18)..(18)
<223> OTHER INFORMATION: A, T, C, or G
<220> FEATURE:
<221> NAME/KEY: misc_feature
<222> LOCATION: (19)..(19)
<223> OTHER INFORMATION: A, T, C, or G
<220> FEATURE:
<221> NAME/KEY: misc_feature
<222> LOCATION: (20)..(20)
<223> OTHER INFORMATION: G, C, or T
<220> FEATURE:
<221> NAME/KEY: misc_feature
<222> LOCATION: (21)..(21)
<223> OTHER INFORMATION: A, T, C, or G
<220> FEATURE:
<221> NAME/KEY: misc_feature
<222> LOCATION: (22)..(22)
<223> OTHER INFORMATION: A, T, C, or G
<220> FEATURE:
<221> NAME/KEY: misc_feature
<222> LOCATION: (23)..(23)
<223> OTHER INFORMATION: G, C, or T
<220> FEATURE:
<221> NAME/KEY: misc_feature
<222> LOCATION: (24)..(24)
<223> OTHER INFORMATION: A, T, C, or G
<220> FEATURE:
<221> NAME/KEY: misc_feature
<222> LOCATION: (25)..(25)
<223> OTHER INFORMATION: A, T, C, or G
<220> FEATURE:
<221> NAME/KEY: misc_feature
<222> LOCATION: (26)..(26)
<223> OTHER INFORMATION: G, C, or T
<220> FEATURE:
<221> NAME/KEY: misc_feature
<222> LOCATION: (27)..(27)
<223> OTHER INFORMATION: A, T, C, or G
<220> FEATURE:
<221> NAME/KEY: misc_feature
<222> LOCATION: (28)..(28)
<223> OTHER INFORMATION: A, T, C, or G
<220> FEATURE:
<221> NAME/KEY: misc_feature
<222> LOCATION: (29)..(29)
<223> OTHER INFORMATION: G, C, or T
<220> FEATURE:
<221> NAME/KEY: misc_feature
<222> LOCATION: (30)..(30)
<223> OTHER INFORMATION: A, T, C, or G
<220> FEATURE:
<221> NAME/KEY: misc_feature
<222> LOCATION: (31)..(31)
<223> OTHER INFORMATION: A, T, C, or G
<220> FEATURE:
<221> NAME/KEY: misc_feature
<222> LOCATION: (32)..(32)
<223> OTHER INFORMATION: G, C, or T

<400> SEQUENCE: 9
gctagaattc nnnnnnnnnn nnnnnnnnnn nnaagcttac tgcagtagca tg        52

<210> SEQ ID NO 10
```

```
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 10
catgctactg cagtaagctt                                              20
```